US005616504A

United States Patent [19]
Brown et al.

[11] Patent Number: 5,616,504
[45] Date of Patent: Apr. 1, 1997

[54] METHOD AND SYSTEM FOR CALIBRATION OF IMMUNOASSAY SYSTEMS THROUGH APPLICATION OF BAYESIAN ANALYSIS

[75] Inventors: Emery N. Brown, Brookline; Steven J. Skates, Cambridge, both of Mass.

[73] Assignee: The General Hospital Corporation, Boston, Mass.

[21] Appl. No.: 370,480

[22] Filed: Jan. 9, 1995

Related U.S. Application Data

[63] Continuation of Ser. No. 21,323, Feb. 23, 1993, abandoned.

[51] Int. Cl.$^6$ .................................................. G01N 33/543
[52] U.S. Cl. ........................ 436/518; 436/545; 436/804; 435/7.1
[58] Field of Search .................................. 436/518, 545, 436/804; 435/7.1; 364/413.02

[56] References Cited

FOREIGN PATENT DOCUMENTS 0368462  5/1990  European Pat. Off. .
0505003  9/1992  European Pat. Off. .

OTHER PUBLICATIONS

Feldkamp, C.S. and Smith, S.W., "Practical Guide to Immunoassay Method Evaluation", Immunoassay: A Practical Guide, (San Diego: Academic Press, 1987), pp. 49–51.
Sadler, W.A. and Smith, M.H., "Estimation of the Response–Error Relationship in Immunoassay", Clin. Chem. vol. 31, No. 11, 1985, pp. 1802–1805.
Seber, G.A.F. and Wild, C.J., "Nonlinear Regression", 1989, pp. 247–250.
Powsner, E.R., "Basic Principles of Radioactivity and its Measurement", In Textbook of Clinical Chemistry, Ed. N.W. Tietz, (Philadelphia: W.B. Saunders, 1986) Sect. 1B–Analytical Procedures and Instrumentation, pp. 173–197.

Baxter, J.D. and Tyrrell, J.B., "The Adrenal Cortex" in Endocrinology and Metabolism, Second Edition, Editors, Felig, Baxter, Broadus and Frohman, pp. 511,610–612, McGraw–Hill, New York 1987.
Williams, G.H. and Dluhy, R.G., "Diseases of the Adrenal Cortex", in Harrison's Principles of Internal Medicine, 12th Ed. vol. 2, (New York: McGraw–Hill, 1991), pp. 1713–1718.

(List continued on next page.)

Primary Examiner—James C. Housel
Assistant Examiner—Rachel Heather Freed
Attorney, Agent, or Firm—Wolf, Greenfield & Sacks, P.C.

[57] ABSTRACT

A method for improved measurement of a concentration of an analyte in a sample having an unknown concentration of the analyte includes using an affinity assay having an experimental indicator. Standard and control samples, each having a known concentration of the analyte are assayed and a response, an amount of experimental indicator emitted for each sample is detected. The unknown sample is also assayed and its response is detected. A prior probability density is supplied for the unknown concentration, along with a model for a standard curve relating an expected response to a concentration of the analyte. A posterior density, having a median, for the unknown concentration is generated based on the supplied prior density, the supplied model, and the responses for the standard samples, the control samples and the unknown samples, by applying Bayes' rule. The median of the posterior density may be provided as the measure of concentration of analyte in the unknown sample, with an accuracy defined by the standard deviation of the posterior density. The standard curve preferably accounts for relative error due to experimental variation by using a random variable to represent variations on the analyte concentration scale due to variability in the preparation of samples in the laboratory. The minimal detectable dose for a single assay run may also be determined.

35 Claims, 16 Drawing Sheets

OTHER PUBLICATIONS

Finney, D.J., "Response Curves for Radioimmunoassay", Clin. Chem. vol. 29, No. 10, 1983, pp. 1762–1766.

Kass, R.E., "Computing Observed Information by Finite Differences" Commun. Statist Simula., vol. 16(2), pp. 587–599 (1987).

Davidian, M., et al., "Variance functions and the minimum detectable concentration in assays", Biometrika (1988), vol. 75, No. 3, pp. 549–556.

Fernandez, A.A., et al., "Interrelations of the Various Mathematical Approaches to Radioimmunoassay", Clin. Chem. vol. 29, No. 2, 1983, pp. 284–289.

Rodbard, D. and Frazier, G.R., "[1] Statistical Analysis of Radioligand Assay Data", Methods in Enzymology, vol. 37, 1975, pp. 3–23.

Lwin, T. and Maritz, J.S., "A Note on the Problem of Statistical Calibration", Applied Statistics, vol. 29, No. (1980), pp. 135–141.

Dunsmore, I.R., "A Bayesian Approach to Calibration", pp. 396–405 Journal of the Royal Statistical Society Series B, vol. 31, No. 2, 1968.

Raab, G.M., "Comparison of a Logistic and a Mass–Action Curve for Radioimmunoassay Data", Clin. Chem. vol. 29, No. 10, 1983, pp. 1757–1761.

Rodbard, D., "Statistical Estimation of the Minimal Detectable Concentration (Sensitivity) for Radioligand Assays", Analytical Biochemistry, vol. 90, pp. 1–12, (1978).

Oppenheimer, L., et al., "Determining the Lowest Limit of Reliable Assay Measurement", Anal. Chem., vol. 55, No. 4, Apr. 1983, pp. 638–643.

Lwin, T. and Maritz, J.S., "An Analysis of the Linear–Calibration Controversy From the Perspective of Compound Estimation", Technometrics, vol. 24, No. 3, Aug. 1982, pp. 235–242.

Ratkowsky, D.A., "Choosing Near–Linear Parameters in the Four–Paremeter Logistic Model for Radioligand and Related Assays", Biometrics, vol. 42, pp. 575–582, Sep. 1986.

Rodbardd, D., et al., "Statistical Characterization of the Random Errors in the Radioimmunoassay Dose–Response Variable", Clin. Chem. vol. 22, No. 3, 1976, pp. 350–358.

de los Santos, E.T., et al., "Sensitivity, Specificity, and Cost–effectiveness of the Sensitive Thyrotropin Assay in the Diagnosis of Thyroid Disease in Ambulatory Patients", Arch. Intern. Med., vol. 149, Mar. 1989, pp. 526–532.

Helfand, M., et al., "Monitoring Therapy in Patients Taking Levothyroxine", Annals of Internal Medicine, vol. 113, No. 6, 15 Sep. 1990, pp. 450–454.

Stall, G.M., et al., "Accelerated Bone Loss in Hypothyroid Patients Overtreated with L–Thyroxine", Annals of Internal Medicine, vol. 113, No. 4, 15 Aug. 1990, pp. 265–269.

Rodbard, D., "Statistical Quality Control and Routine Data Processing for Radioimmunoassays and Immunoradiometric Assays", Clin. Chem. vol. 20, No. 10, 1974, pp. 1255–1270.

Finney, D.J., "Radioligand Assay", Biometrics, vol. 32, pp. 721–740, Dec. 1976.

Drake, A.W., "Fundamentals of Applied Probability Theory", pp. 133–147, 229–257, McGraw–Hill Book Co., 1967.

Mosteller, F. et al., "Inference and Disputed Authorship: The Federalist", p. 154, Addison–Wesley Publishing Co., Inc., Reading, MA, 1964.

Press, S.J, "Bayesian Statistics: Principles, Models, and Applications", pp. 80 & 83, John Wiley & Sons, New York, 1989.

Skates, S.J., "Laplacian and Uniform Expansions with Applications to Multidimensional Sampling", PhD Thesis, Dept. of Statistics, The University of Chicago, Chicago, IL, Aug. 1987.

Smith, A.F.M. et al., "Bayesian Computation via the Gibbs Sampler and Related Markov Chain Monte Carlo Methods", J.R. Statist. Soc. B (1993), vol. 55, No. 1, pp. 3–23.

Borth, Proceedings of the Karolinska Symposia on Research Methods in Reproductive Technology, Mar. 23–25, 1970, Acta Endocrinologica, Supplementum 147, (1970), pp. 30–36.

GammaCoat [125I] Cortisol Radioimmunoassay Kit, Cat. No. CA–529, CA–549 Instruction Set, DADE, Baxter Travenol Diagnostics, Inc., Cambridge, MA, Jul. 1987.

Xiapoing Hu et al., "Bayesian Image Processing in Magnetic Resonance Imaging", Magnetic Resonance Imaging, vol. 9, 1991, pp. 611–620.

N.R. Draper et al., "1.7 Inverse Regression (Straight Line Case)" Applied Regression Analysis, New York: John Wiley & Sons, Inc., 1966, pp. 47–51.

D. Rodbard, "Data Processing for Radioimmunoassays: An Overview", In Clinical Immunochemistry, Ed. S. Natelson et al., Washington: American Association for Clinical Chemistry, pp. 477–494.

C.D. litton and M.N. Leese, "Some Statistical Problems Arising In Radiocarbon Calibration," Journal of Archaeological Science, vol. 16, pp. 101–109.

C.E. Buck, C.D. Litton and A.F.M. Smith, "Calibration of Radio–Carbon results Pertaining To Related Archaeological Events," Journal of Archaelogical Science vol. 19, (1992) pp. 497–512.

J. Sambrook, E.F.Fritsch, T.Maniatis, "Molecular Cloning," A Laboratory Manual, Second Edition, Cold Spring Harbor Laboratory Press, 1989, pp. 18.19–18.23.

J.C. Naylor and A.F.M.Smith, "An Archaeological Inference Problem," Journal of the American Statistical Association, vol. 83, No. 403, Sep. 1988, pp. 588–595.

Minze Stuiver and Gordon W. Pearson, "High–Precision Calibration Of The Radiocarbon Time Scale, AD 1950–500 BC," Radiocarbon, vol. 28, No. 2B, 1986, pp. 805–838.

Minze Stuiver and Gordon W. Pearson, "High–Precision Calibration Of The Radiocarbon Time Scale, 500–250 BC," Radiocarbon, vol. 28 No. 2B, 1986, pp. 839–862.

Fernandez, A.A. Clin. Chem. 29(2):284–289 1983.

Hu, X.P. Magn Reson Imaging 9(4):611–20 1991.

TABLE 1. COUNTS FOR CORTISOL STANDARDS, CONTROLS, UNKNOWNS AND THEIR APPROXIMATE Z-STATISTICS

| DOSE | COUNT | STANDARDS COUNT | Z-STATISTIC |
|---|---|---|---|
| 0.0 | 18747 | 19870 | -8.08 |
| 1.0 | 17237 | 17496 | -1.97 |
| 3.0 | 13413 | 14311 | -7.63 |
| 10.0 | 9857 | 9203 | 6.70 |
| 25.0 | 5744 | 5903 | -2.08 |
| 60.0 | 3326 | 3346 | -0.35 |

| DOSE | COUNT | CONTROLS COUNT | Z-STATISTIC |
|---|---|---|---|
| 3.6 | 13144 | 12567 | 5.08 |
| 18.5 | 6226 | 6319 | -1.17 |
| 29.5 | 5735 | 4667 | 14.08 |

| COUNT | UNKNOWNS COUNT | Z-STATISTIC |
|---|---|---|
| 5784 | 5844 | -0.78 |
| 6683 | 6864 | -2.20 |
| 5012 | 5590 | -7.94 |
| 6785 | 6724 | 0.74 |
| 6387 | 6345 | 0.53 |
| 11034 | 10802 | 2.22 |
| 5874 | 5323 | 7.36 |
| 3763 | 4161 | -6.32 |
| 4939 | 5064 | -1.77 |
| 13581 | 13853 | -2.32 |

FIG. 11

TABLE 2. MODEL PARAMETER ESTIMATES, STANDARD ERRORS AND THE ESTIMATES OF THE OBSERVED INFORMATION PARTITIONED AMONG THE STANDARDS, CONTROLS AND THE UNKNOWNS

| MODEL PARAMETERS | ESTIMATES (STANDARD ERRORS) | TOTAL INFORMATION | INFORMATION IN STANDARDS (PERCENTAGE) | INFORMATION IN CONTROLS (PERCENTAGE) | INFORMATION IN UNKNOWNS (PERCENTAGE) |
|---|---|---|---|---|---|
| MAX | 21,161.25 (992.04) | $3.593 \times 10^{-5}$ | $2.897 \times 10^{-5}$ (80.63%) | $6.903 \times 10^{-6}$ (19.21%) | $5.455 \times 10^{-8}$ (0.16%) |
| $\beta$ | -1.483 (0.20) | $2.467 \times 10^{3}$ | $1.517 \times 10^{3}$ (61.50%) | $9.495 \times 10^{2}$ (38.50%) | $1.033 \times 10^{-6}$ (0.00%) |
| $\gamma$ | -0.791 (0.079) | $8.594 \times 10^{3}$ | $1.020 \times 10^{3}$ (11.87%) | $7.412 \times 10^{3}$ (86.24%) | $1.623 \times 10^{2}$ (1.89%) |
| MIN | 324.25 (692.65) | $7.699 \times 10^{-5}$ | $5.107 \times 10^{-5}$ (66.34%) | $2.583 \times 10^{-5}$ (33.55%) | $8.620 \times 10^{-8}$ (0.01%) |
| $\sigma$ | 0.097 (0.047) | $4.777 \times 10^{3}$ | $1.640 \times 10^{3}$ (34.33%) | $2.059 \times 10^{3}$ (43.10%) | $1.078 \times 10^{3}$ (22.57%) |

FIG. 12

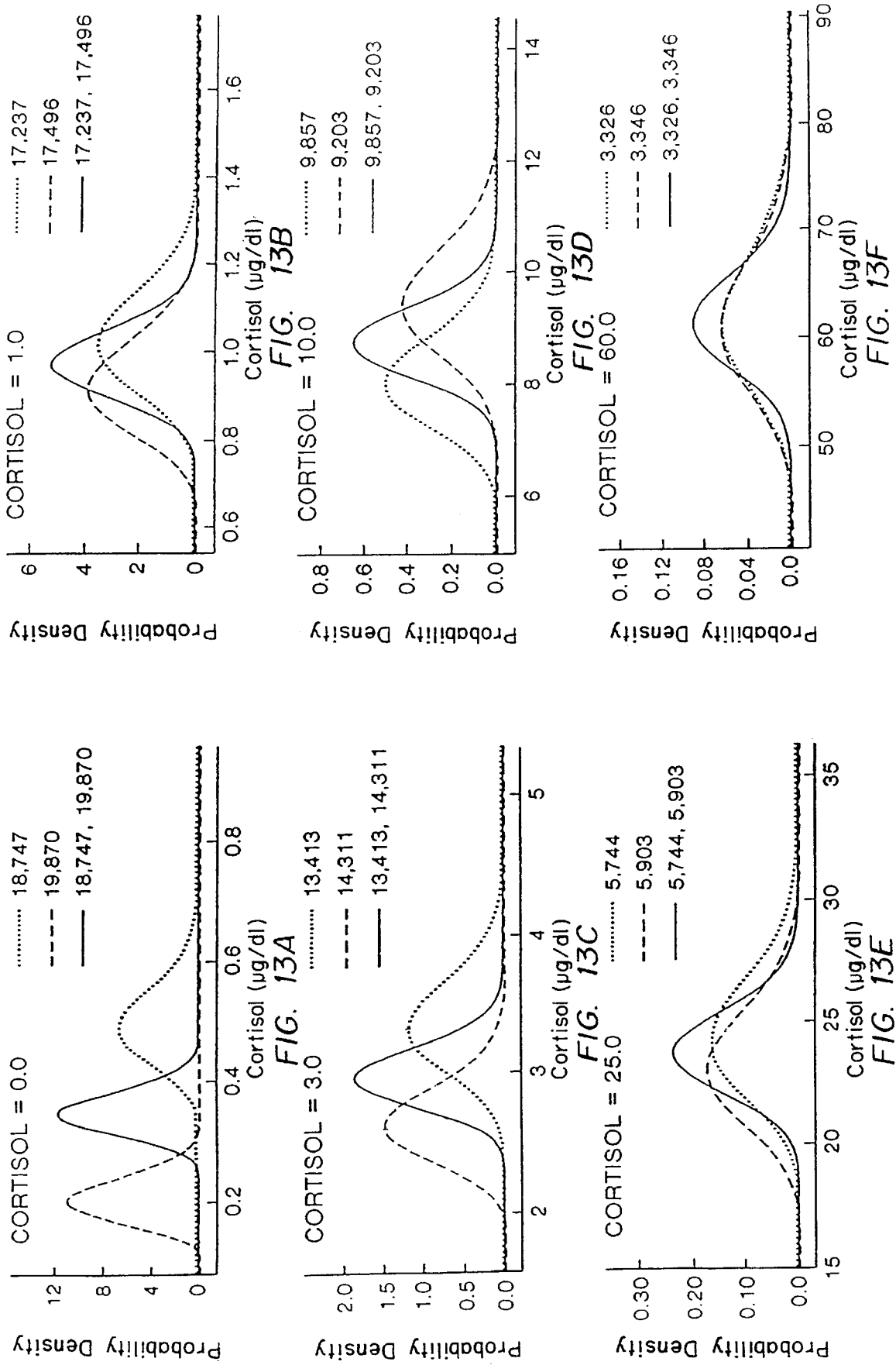

TABLE 3. SUMMARY STATISTICS FOR THE POSTERIOR DENSITIES
OF THE CORTISOL STANDARDS AND CONTROLS

STANDARDS: SINGLE COUNTS

| DOSE | COUNT | MEDIAN | MODE | MEAN | SD | CV(X 100%) |
|---|---|---|---|---|---|---|
| 0.0 | 18747 | 0.497 | 0.490 | 0.501 | 0.064 | 12.7 |
| 0.0 | 19870 | 0.207 | 0.202 | 0.209 | 0.037 | 17.9 |
| 1.0 | 17237 | 1.027 | 1.014 | 1.033 | 0.114 | 11.1 |
| 1.0 | 17496 | 0.923 | 0.912 | 0.929 | 0.104 | 11.2 |
| 3.0 | 13413 | 3.358 | 3.321 | 3.375 | 0.344 | 10.2 |
| 3.0 | 14311 | 2.642 | 2.613 | 2.656 | 0.273 | 10.3 |
| 10.0 | 9857 | 8.081 | 7.988 | 8.121 | 0.815 | 10.0 |
| 10.0 | 9203 | 9.491 | 9.382 | 9.539 | 0.956 | 10.0 |
| 25.0 | 5744 | 24.415 | 24.212 | 24.538 | 2.460 | 10.0 |
| 25.0 | 5903 | 23.233 | 23.040 | 23.349 | 2.340 | 10.0 |
| 60.0 | 3326 | 61.931 | 61.200 | 62.249 | 6.313 | 10.0 |
| 60.0 | 3346 | 61.326 | 60.603 | 61.641 | 6.250 | 10.1 |

STANDARDS: PAIRED COUNTS

| DOSE | COUNT | COUNT | MEDIAN | MODE | MEAN | SD | CV(X 100%) |
|---|---|---|---|---|---|---|---|
| 0.0 | 18747 | 19870 | 0.348 | 0.345 | 0.350 | 0.035 | 10.0 |
| 1.0 | 17237 | 17496 | 0.974 | 0.969 | 0.977 | 0.077 | 7.9 |
| 3.0 | 13413 | 14311 | 2.982 | 2.971 | 2.989 | 0.216 | 7.2 |
| 10.0 | 9857 | 9203 | 8.758 | 8.713 | 8.780 | 0.622 | 7.1 |
| 25.0 | 5744 | 5903 | 23.817 | 23.695 | 23.876 | 1.690 | 7.1 |
| 60.0 | 3326 | 3346 | 61.627 | 61.308 | 61.785 | 4.425 | 7.2 |

CONTROLS: SINGLE COUNTS

| DOSE | COUNT | MEDIAN | MODE | MEAN | SD | CV(X 100%) |
|---|---|---|---|---|---|---|
| 3.6 | 13144 | 3.599 | 3.559 | 3.618 | 0.368 | 10.2 |
| 3.6 | 12567 | 4.124 | 4.117 | 4.130 | 0.422 | 10.1 |
| 18.5 | 6226 | 21.061 | 20.886 | 21.166 | 2.120 | 10.0 |
| 18.5 | 6319 | 20.486 | 20.316 | 20.589 | 2.062 | 10.0 |
| 29.5 | 5735 | 24.485 | 24.281 | 24.607 | 2.467 | 10.0 |
| 29.5 | 4667 | 35.181 | 34.886 | 35.358 | 3.555 | 10.1 |

CONTROLS: PAIRED COUNTS

| DOSE | COUNT | COUNT | MEDIAN | MODE | MEAN | SD | CV(X 100%) |
|---|---|---|---|---|---|---|---|
| 3.6 | 13144 | 12567 | 3.873 | 3.856 | 3.883 | 0.278 | 7.2 |
| 18.5 | 6226 | 6319 | 20.772 | 20.667 | 20.823 | 1.473 | 7.1 |
| 29.5 | 5735 | 4667 | 29.334 | 29.195 | 29.408 | 2.085 | 7.1 |

FIG. 15

TABLE 4. SUMMARY STATISTICS FOR THE POSTERIOR DENSITIES OF THE
CORTISOL UNKNOWNS AND THE MINIMAL DETECTABLE DOSE

UNKNOWNS: PAIRED COUNTS

| COUNT | COUNT | MEDIAN | MODE | MEAN | SD | CV(X 100%) |
|---|---|---|---|---|---|---|
| 5784 | 5844 | 24.885 | 23.765 | 23.945 | 1.695 | 7.1 |
| 6683 | 6864 | 17.961 | 17.870 | 18.006 | 1.273 | 7.1 |
| 5012 | 5590 | 28.235 | 28.137 | 28.306 | 2.006 | 7.1 |
| 6785 | 6724 | 18.057 | 17.967 | 18.102 | 1.280 | 7.1 |
| 6387 | 6345 | 20.204 | 20.103 | 20.255 | 1.433 | 7.1 |
| 11034 | 10802 | 6.244 | 6.214 | 6.259 | 0.445 | 7.1 |
| 5874 | 5323 | 25.608 | 25.443 | 25.672 | 1.818 | 7.1 |
| 3763 | 4161 | 46.473 | 46.161 | 46.591 | 3.320 | 7.1 |
| 4939 | 5064 | 31.216 | 31.056 | 31.295 | 2.220 | 7.1 |
| 13581 | 13853 | 3.101 | 3.087 | 3.109 | 0.224 | 7.2 |

MINIMAL DETECTABLE DOSE

| MEDIAN | MODE | MEAN | SD | CV(X 100%) |
|---|---|---|---|---|
| 0.4548 | 0.4510 | 0.4575 | 0.0421 | 9.2 |

FIG. 16

METHOD AND SYSTEM FOR CALIBRATION OF IMMUNOASSAY SYSTEMS THROUGH APPLICATION OF BAYESIAN ANALYSIS

This application is a continuation of application Ser. No. 08/021,323, filed on Feb. 23, 1993, now abandoned.

FIELD OF THE INVENTION

The invention is related to computer systems and methods used with an affinity assay to measure an analyte concentration and to determine the accuracy of such a measurement.

BACKGROUND OF THE INVENTION

Affinity assays are important measurement tools used in clinical and research laboratories for determining the concentration of an analyte in a sample. The term "analyte" refers broadly to any substance (a ligand) capable of being detected by formation of a complex with a corresponding anti-ligand. Such complex formation is an integral part of various classes of affinity assays, including for example, immunoassays (such as radioimmunoassays and immunoradiometric assays) and protein-binding assays (such as radioreceptor assays). Thus, the analyte may be an antigen or antibody in an immunoassay, or a protein or its cognate in a protein-binding assay.

Such assays may take a variety of formats. In a direct assay format, a complex is formed between the analyte and the anti-ligand. In an indirect assay format such as a competitive assay, a complex is formed between a competitor and the anti-ligand. The competitor competes with the analyte for specific attachment to the anti-ligand.

To detect the presence of an analyte using an affinity assay, one of the members of a complex is labelled with a tag which is capable of being detected. Examples of classes of such tags include radioisotopes, e.g. 125-[I]; enzymes, e.g., horse radish peroxidase; fluorescent compounds; bioluminescent compounds, e.g., luciferin; and chemiluminescent compounds, e.g., acridinium esters. Each tag emits a corresponding experimental indicator, such as gamma radiation, light, fluorescent light or enzyme activity, which may be detected.

The response, i.e., the amount of experimental indicator detected, for a given concentration of analyte in a sample varies probabilistically. This variation is known as response error, and is Poisson for gamma radiation and is either Normal or log-Normal for the other types of experimental indicators noted above. The amount of variation may change with the mean level of the response. For a given concentration of analyte in a sample the response may also vary due to variation in the performance of the assay from one assay run to the next or due to variation in the preparation of the assayed samples. This variation may be due to errors in pipetting or mixing, incomplete separation between bound and unbound sample components, variation in reagent quality, or variation in response measurement time, incubation, temperature or centrifuging conditions. This variation introduces a random error in the concentration of the analyte. The relative error due to such experimental variation is experimental error.

Because of both response error and experimental error, measuring the concentration of an analyte in a sample using an affinity assay involves an application of formal statistical analysis based on the responses from data from a number of samples, which ensures accurate data interpretation and maintains quality control. Statistical analysis is also used to determine the accuracy of an inferred concentration.

Conventionally, using an affinity assay to measure an unknown concentration of analyte in a sample involves analyzing three sets of samples: standard samples, control samples, and the unknown analyte sample. Standard samples are prepared by the assay kit manufacturer in accordance with World Health Organizations (WHO) or the United States National Bureau of Standard (USNBS) specifications and contain known concentrations of the analyte, spanning the range of concentrations which are sufficient to establish a standard curve from which the concentration of the unknown sample can be inferred. Preferably, this range includes the concentrations which are believed to be important. The control samples contain known concentrations of the analyte and are used to chart assay stability and experimental error. Typically, the controls are prepared from samples assayed previously in the current laboratory.

Typically, a large number of unknown samples are assayed together with the standards and controls in what is commonly called a single assay run. In a single assay run, standard samples are assayed first in replicate to obtain a measurement of an amount of the experimental indicator (i.e., a response) by each replicate. For example, with a radioligand binding assay the number of radioactive counts emitted in a given time period by each sample and its replicate is recorded. A standard curve, which relates a known concentration of analyte to an expected response, is estimated, in a manner to be described in more detail below, based on only the known concentrations and corresponding responses for the replicates of the standard samples.

The samples containing unknown concentrations of analyte are then assayed, typically in replicate, along with replicates of the control samples interspersed between the unknown samples. The perception that better quality control can be achieved by automated assay procedures, the rising cost of assaying large numbers of samples and the desire to reduce radioactive waste (resulting from assays using radioisotopes) production have led many laboratories to assay unknown samples as singlets, not replicates. The response for each unknown and control sample replicate is recorded. The analyte concentration in each unknown sample is inferred by finding the ordinate on the estimated standard curve which has the response for the unknown sample as its abscissa.

The standard curve is conventionally estimated by fitting a curve to the known concentrations for the replicates of only the standard samples and their associated responses using a non-linear, weighted least squares technique. The curve has empirically been found to correspond to a four-parameter logistic model (4-PL). This curve sometimes approximates the curve described by the mass-action law for the underlying chemical reaction.

A conventional model used for estimating the standard curve may be described in the following manner:

Let H denote a concentration of analyte and let $h=\log H$. The log scale is commonly used to describe many analyte concentrations since the biologically possible range of concentrations often covers several orders of magnitude. Let Y be the response recorded from assaying sample. For notational purposes, the control, the standard and the unknown samples are denoted respectively as groups 1, 2 and 3. Let $N_i$ be the number of samples in group i, $H_i=[H_{i,1}, \ldots, H_{i,Ni}]^T$ be the analyte concentrations in the $i^{th}$ group samples, $h_i=[h_{i,1}, \ldots, h_{i,Ni}]^T$ be the log analyte concentrations of the $i^{th}$ group samples and let $$Y_i = \begin{vmatrix} Y_{i;1,1} & & Y_{i;N_1,1} \\ & \ldots & \\ Y_{i;1,q} & & Y_{i;N_i,q} \end{vmatrix} \quad (1)$$

be respectively the $N_i \times q$ matrix of measurements obtained from measuring the amount of experimental indicator emitted by the samples assayed in group i, for i=1,2,3, where q is the number of replicates (usually 1 or 2).

In an immunoassay or protein-binding assay, the expected measure of experimental indicator is usually a monotonic function of the analyte concentration, to which a four parameter logistic (4-PL) model has been found empirically to fit well. A parametrization of the 4-PL model is:

$$E(Y|h, \Theta) = \frac{\max - \min}{1 + \exp(\beta - \gamma h)} + \min = g(h, \Theta) \quad (2)$$

where $\Theta = [\max, \gamma, \beta, \min]^T$. Other parametrizations are also well-known. If $\epsilon$ is set to be $-\gamma$, with $\rho = \exp(\beta/\gamma)$, and $\Theta^* = [\max, \epsilon, \rho, \min]^T$ then (2) may be rewritten as $$g(H, \Theta^*) = \frac{\max - \min}{1 + \left(\frac{H}{\rho}\right)\epsilon} + \min \quad (3)$$

which is the conventional "Rodbard" model. See either "Statistical Analysis of Radioligand Assay Data," *Methods in Enzymology*, Volume 37, 1975, pp. 3–22, by D. Rodbard and G. R. Frazier ("Rodbard") or "Radioligand and Assay,", *Biometrics*, Volume 32, 1976, pp. 721–740, by D. J. Finney ("Finney 1976") for a description of this model. These references and all others cited in this document, are expressly incorporated by reference. A graph representing equation (2) is shown in FIG. 1, where the ordinate represents the concentration H and the abscissa represents the expected measure E(Y).

The 4-PL model is useful because it seems to fit empirically the mass-action law equations governing the kinetics of some affinity assays under some conditions which have been described in the art. See, for such a description, "Interrelations of the various mathematical approaches to radioimmunoassay," *Clinical Chemistry*, Volume 29, 1983, pp. 284–289, by A. A. Fernandez et al. ("Fernandez"), or "Response curves for Radioimmunoassay," *Clinical Chemistry*, Vol. 29, 1983, pp. 1762–1766, by D. J. Finney ("Finney 1983") or "A Comparison of Logistic and Mass-Action Curves for Radioimmunoassay Data," in *Clinical Chemistry*, Vol. 29, 1983, pp. 1757–1761 ("Raab").

After a standard curve is estimated using the measured responses for the standard samples, a concentration of analyte is estimated for each of the unknown samples using the estimated standard curve. The average concentration of replicates, computed from the individual estimates, is reported as the estimated concentration in the unknown sample, provided that the individual estimates do not differ appreciably from each other.

The average and the standard deviation of the individual estimated concentrations for the replicates of an unknown sample are used to compute the intra-assay coefficient of variation for the estimated analyte concentration. That is, they are used to quantify a measure of accuracy of the estimate. The estimates of the concentrations for the control samples are used to compute the intra-assay coefficients of variation at selected concentrations throughout the range of the assay. The inter-assay coefficients of variation are computed from the estimated concentrations for the control samples obtained from different assay runs.

Nearly every laboratory in the world which uses affinity assays uses some form of the method described above.

However, several theoretical and practical problems with this method exist.

First, for most assays the experimental error is neither routinely nor formally assessed on the analyte concentration scale. One current approach to accounting for variations in the response beyond that due to expected response error from known physical properties of the tag is to model all variation in the response data as a simple polynomial function of the expected response for a given analyte concentration, i.e. as response error. If the polynomial order is one and there is no constant term, the data contains only response error, whereas if it greater than one, there is extra response variation (either Poisson or Gaussian) as well. For many radioligand binding assays the best choice of exponent has been found to lie between one and two (See Finney 1976).

Rodbard also suggests the "relative error model" as a method for studying the effect of experimental variation on the extra-Poisson variation in the response data of a radioligand binding assay. See also "Statistical aspect of radioimmunoassay," by D. Rodbard, in *Principles of Competitive Protein Binding Assays,* Ed. W. D. Odell et al., Philadelphia: Lippincott, 1971, pp. 204–259, ("Rodbard 1971"), for a similar suggestion. With this method, any experimental variation is represented by an estimate of the amount of extra-Poisson variation in the observed measure of radioactivity of the standards as determined by the type of weights used in fitting the standard curve with nonlinear regression methods. Thus, experimental variation is modelled in terms of the response instead of explicitly as error in the concentration of the samples being assayed.

It is important to estimate experimental variation because it affects the measurement accuracy of all unknown samples, and gives information to laboratory personnel concerning the consistency and quality of materials and technique. Because of the manner in which experimental variations are considered by models used in these methods, experimental error cannot be accurately determined on the analyte scale.

A second problem with conventional methods is that it is not possible to obtain a reasonable determination of the accuracy of the estimated analyte concentration for a singlet. Therefore replicate unknown samples must be assayed.

Third, because both the response and the concentration of analyte are random variables, directly inverting the estimated standard curve describing the expected response for a given analyte concentration does not describe correctly the expected analyte concentration for a given response. See *Non-linear Regression,* by G. A. F. Seber and C. J. Wild, (New York: John Wiley & Sons), 1989, pp. 247–250 ("Seber"). Although any resulting inaccuracy in concentration estimates is minimal, the effect of this inaccuracy on the determination of the accuracy of these estimates is substantial, as described below.

Fourth, because the minimal detectable dose (MDD) is not determined as part of a single assay run, a predetermined MDD does not correctly represent the smallest quantity of analyte detectable by a given assay run. The assay MDD or sensitivity (defined as the smallest analyte concentration which the assay can just distinguish from an apparent blank concentration) is usually determined when the assay is first prepared by assaying a large number, e.g., 20 to 40, of replicates of samples with an apparent blank concentration (blank samples). With conventional assay procedures, the standard curve is estimated for a single assay run from ten to twelve observations, i.e., with five or six standards each assayed in duplicate, of which only one standard, and thus two observations, are from blank samples. Because the MDD is predetermined using a number of standards far in excess of the number used on a day-to-day basis in the laboratory, it cannot reliably be used as the MDD for a single assay run. Instead, the practice in many laboratories is to report only the analyte concentrations which exceed that of the smallest non-blank standard sample.

The definition of the MDD provided by Rodbard 1978 is a conventional approximation to the upper limit of the $1 - \alpha$ highest probability density (HPD) interval, where $\alpha$ is between 0 and 1, for the apparent blank analyte concentration and as such, considers the uncertainty in the determination of the apparent blank analyte concentration. However it does not consider the uncertainty in any other analyte concentrations. For further discussions of the MDD see "Statistical estimation of the minimal detectable concentration for radio immunoassays" by D. Rodbard in *Analytical Chemistry*, Vol. 90, 1978, pp. 1–12, ("Rodbard 1978"); "Determining the lowest limit of reliable assay measurement," by L. Oppenheimer et al., in Analytical Chemistry, Vol. 55, 1983, pp. 638–643 ("Oppenheimer"); "Variance functions and minimal detectable concentration in assays," in *Biometrika*, Volume 75, Number 3, 1988, pp. 549–556, by M. Davidian et al. ("Davidian").

Finally, the validity of the estimation of accuracy obtained using conventional methods is questionable. While conventional methods allow for a systematic analysis of data, these methods rely on and are derived from large sample theory. The validity of inferences for affinity assays using large sample approximations is questionable since most standard curves are estimated from not more than a dozen observations, not from a large sample. This problem has been discussed in the art. See, for example, Davidian.

Despite these problems, all laboratories currently use these conventional methods. An alternative method for obtaining an estimated concentration for an unknown sample, the application of Bayes' rule, has been suggested in "A Note on the Problem of Statistical Calibration" by T. Lwin and J. S. Maritz in *Applied Statistics*, Volume 29, pp. 135–141, 1980 ("Lwin"). To use Bayes' rule, a specification of a prior distribution for the analyte concentration in the unknown sample is required. However, the prior density specified by Lwin has been discredited as unrealistic for practical applications. (See Seber, p. 248). The prior density specified by Lwin is particularly unrealistic for use in measuring analyte concentrations using affinity assays.

A Bayesian approach to the estimation and use of a standard curve has been discussed generally in "A Bayesian Approach to Calibration" by I. R. Dunsmore, *Journal of the Royal Statistical Society*, Series B, Volume 31, pp. 396–405, 1968 ("Dunsmore"). However, in the standard curve described in Dunsmore, the expected response is assumed to be directly proportional to the quantity to be estimated. As such it is wholly inapplicable and too simplistic for affinity assays, for which a standard curve is typically described by a sigmoid fraction, such as the 4-PL model.

SUMMARY OF THE INVENTION

A method for measuring a concentration of an analyte in a sample having an unknown concentration of the analyte in accordance with the invention involves using an affinity assay having an experimental indicator. Standard and control samples, each having a known concentration of the analyte are assayed and an amount of experimental indicator emitted by each sample is detected. The unknown sample is also assayed and its response is detected. A prior probability density is supplied for the unknown concentration, along with a model for a standard curve relating an expected response to a concentration of the analyte. A posterior density, having a median, for the unknown concentration is generated based on the supplied prior density, the supplied model, and the responses for the standard samples, the control samples and the unknown samples, by applying Bayes' rule. The median of the posterior density may be provided as the measure of concentration of analyte in the unknown sample. In some instances, the mean or mode may be used as the estimate. The accuracy of an estimate is fully specified by the posterior density. A summary of this accuracy could be provided by the coefficient of variation, the standard deviation or other summaries of the dispersion of the posterior density.

In one aspect of the invention, the posterior density is determined using estimated parameters for the model of the standard curve. These estimates may be determined using a weighted least-squares technique or by using maximum likelihood estimation. The parameters for the standard curve may be derived using only the standard samples, as is done conventionally, or by using all of the samples, including unknown samples.

The model of the standard curve may be based on the mass-action law for the underlying chemical reaction or on a 4-PL model. The model is preferably augmented to account for relative error due to experimental variation. Such an augmentation is preferably done by using a random variable to represent variations on the analyte concentration scale due to variability in the preparation of samples in the laboratory. This random variable may be a Gaussian random variable, resulting in a probability density for the response for a given concentration which is a Gaussian mixture of random variables. In the case of a radioligand binding assay, this probability density is a Gaussian mixture of Poisson random variables.

In another aspect of the invention, the parameters of the standard curve are integrated out to account for all uncertainty in these parameters while deriving the inference for the concentration of an unknown sample.

In another aspect of the invention, the minimal detectable dose for a single assay run is determined by determining the posterior density for apparently blank standard samples $H_{y|0}$ along with a 1-$\alpha$ highest probability density (HPD) interval where $0<\alpha<1$, such as a 95% HPD interval. The set E of random variables $H_y$ which satisfy the condition that zero is the left endpoint of the 1-$\alpha$ HPD interval of the random variable $H_y$-$H_{y|0}$ is determined. The minimal detectable dose of the assay run is the supremum of the set of medians for the probability densities of the random variables $H_y$ in set E.

One embodiment of the invention is a computer system for calibrating an assay, to enable an inference about an analyte concentration in a sample based on a measurement of an experimental indicator emitted from assayed samples, and to determine the accuracy of the inference, the minimal detectable concentration of an assay run, and to measure and separate the variation due to experimental materials and technique from response variation.

The type of detector to be used is dependent on the type of experimental indicator for the assay. For example, a luminometer is used to detect chemiluminescence or bioluminescence. A spectrophotometer is typically used to detect fluorescence. A gamma detector is used to detect radioactivity. Several detectors are capable of detecting enzyme activity including colorimeters. The selection of an appropriate detector depends on how any enzyme product is to be measured.

BRIEF DESCRIPTION OF THE DRAWING

In the drawing,

FIG. 11 is a table of sample data of an assay for cortisol;

FIG. 12 is a table of model parameter estimates for the example of an assay for cortisol;

FIG. 13A–FIG. 13F are graphs representing the posterior density of the cortisol standards;

FIG. 15 is a table of the summary statistics of the densities shown in FIGS. 13 and 14.

FIG. 16 is a table of the summary statistics for the posterior or densities for the unknowns and the MDD.

DETAILED DESCRIPTION

The present invention will be more completely understood through the following detailed description which should be read in conjunction with the attached drawing in which similar reference numbers indicate similar structures. For the sake of simplicity this description is provided in the context of radioligand binding assays. However, the invention is not limited solely to such assays.

Throughout this description, the following notation, and the notation used in the Background section, will be used: Let [x] denote the probability density of the random variable x, let $P(x|\lambda)$ denote the probability of the Poisson random variable x with mean $\lambda$ and let $\phi(x|\mu,\sigma^2)$ denote specifically the density of a Gaussian random variable with mean $\mu$ and variance $\sigma^2$.

Using an affinity assay to measure the concentration of an analyte in an unknown sample involves well-known techniques used in many laboratories throughout the world, as discussed above. For each sample, a response for a sample is measured by detecting with an appropriate detector the amount of experimental indicator emitted by the sample. Appropriate detectors are well-known devices which provide an output indicative of the measured response.

Figure 1:
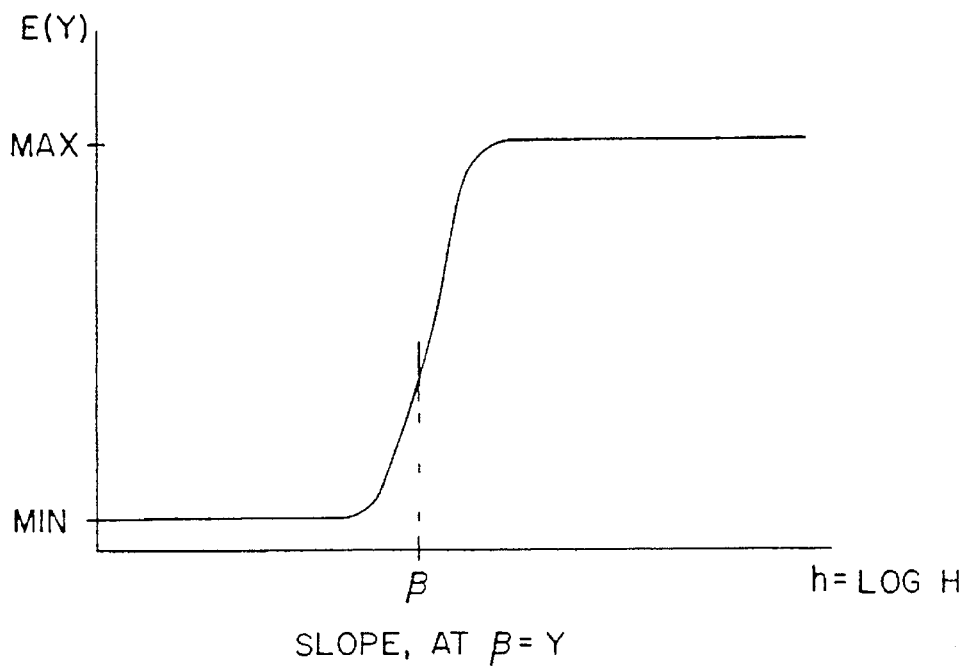
FIG. 1 is a graph of an estimated standard curve according to a four parameter logistic model.
Figure 2:
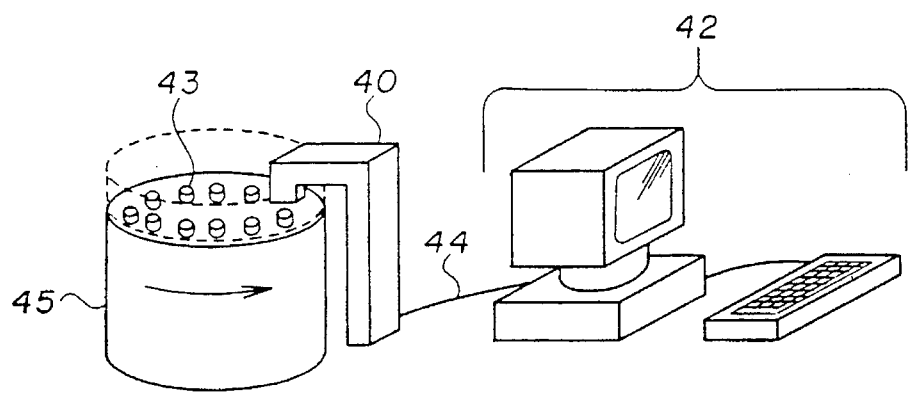
FIG. 2 illustrates a typical arrangement of an affinity assay used with a computer to perform statistical analysis.

As shown in FIG. 2, a detector 40 has its output signal fed to a computer 42 via a cable 44. In a typical arrangement, the detector 40 is arranged so that it is enclosed with a number of samples, in test tubes 43, in a rotatable container 45. Each test tube 43 is placed under the detector 45 for a predetermined amount of time, typically sequentially, by periodically rotating the container 45. Many other arrangements for running the assay may be used, which are well-known in the art.

The kind of detector 40 to be used is dependent on the type of experimental indicator for the assay. For example, a luminometer is used to detect chemiluminescence or bioluminescence. A spectrophotometer is typically used to detect fluorescence. A gamma detector is used to detect radioactivity. Several detectors are capable of detecting enzyme activity including colorimeters. The selection of an appropriate detector depends on how any enzyme product is to be measured. The connection of a detector 40 to a computer 42 can be done in any of many well-known ways so that the computer can store and process the signals from the detector 40.

Figure 3:
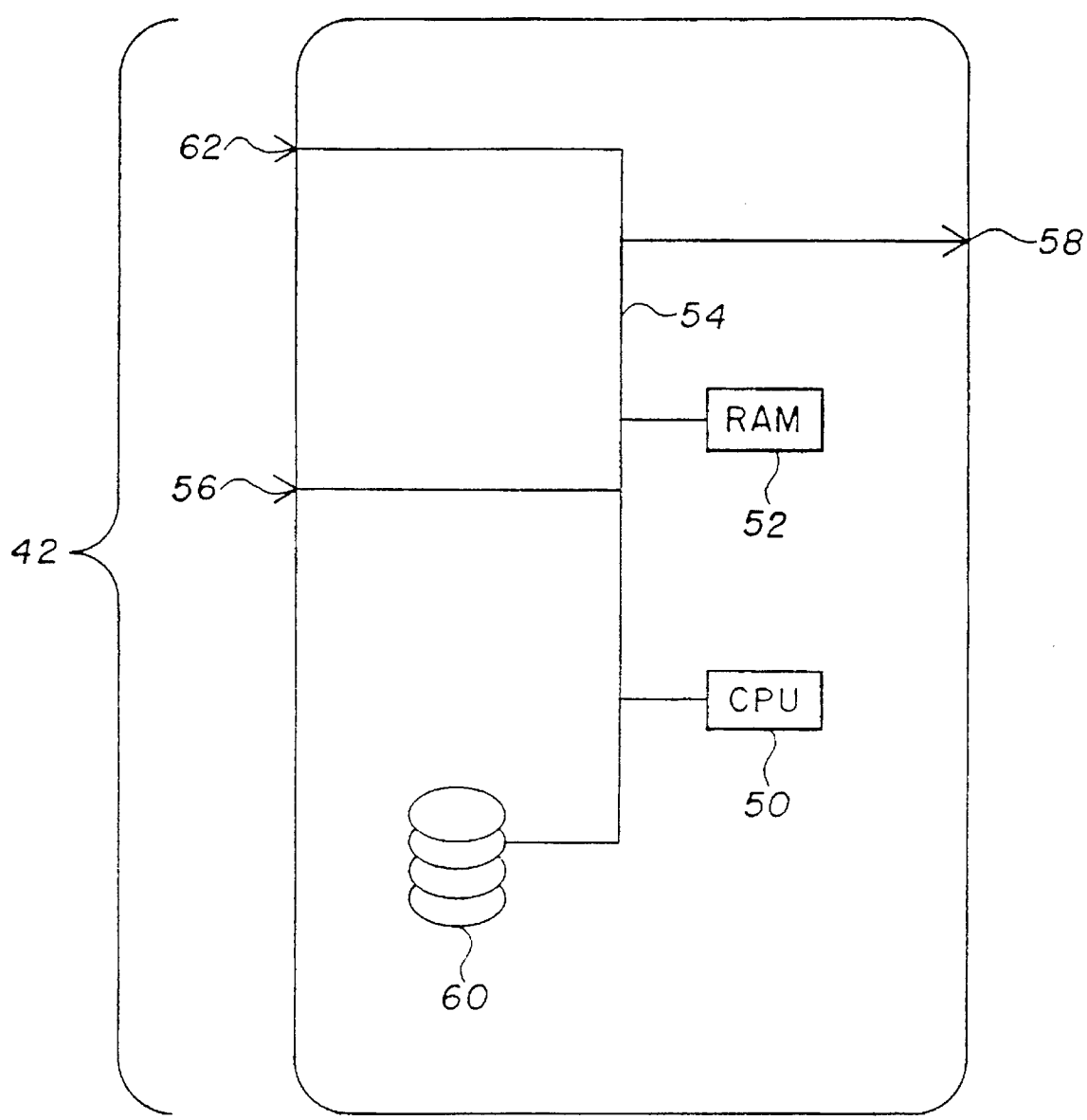
FIG. 3 is a block diagram of a computer which may be used to analyze assay data.

The computer 42 is used to perform statistical analysis on the responses obtained for the samples for each assay run in order to obtain meaningful results from the assay. FIG. 3 is a block diagram of a computer which is suitable for this purpose. Such a computer includes a central processing unit (CPU) 50 and a memory 52, typically a random access memory (RAM), interconnected by a bus 54. The computer also has input and output connections 56 and 58, also connected to the bus, which allow the computer 42 to communicate with output devices (not shown), such as a display or printer, and input devices, such as a keyboard, trackball, mouse, light pen, etc. Numerous other connections to the bus 54 may be provided to allow the computer to connect to other computers (not shown) via a network (not shown). The computer may also include a nonvolatile storage 60, such as a hard disk, to enable storage of large amounts of data for extended periods of time. The computer is also connected to the detector 40 using an input connection 62.

The applicants have implemented a system on an IBM-PC type computer, which has an Intel 80386 microprocessor as its CPU 50. The system has also been implemented on a workstation manufactured by SUN Microsystems of Cupertino, Calif. The system is preferably implemented using standard computer programming techniques to implement statistical analysis procedures as will be described in more detail below. For this purpose, the programming language FORTRAN was used. Standard programs may be used to control the input of data into the computer 42 from the detector 40. To assist development of the computer program for statistical analysis, a library of mathematical sub-routines may be used to perform a number of standard mathematical functions. A suitable library of routines is the International Mathematical Standards Library (IMSL) *Math/Library of FORTRAN Sub-routines for Mathematical Applications,* available from IMSL of Houston, Tex.

It should be understood that the specific computer languages and computer systems shown and described here do not limit the present invention. Many other computer systems, programming languages and programming techniques may be used to practice the present invention.

The statistical analysis of assay data will now be described with reference to the flow chart illustrated in FIG.

4. The computer may be programmed to execute the steps of this method.

Figure 4:
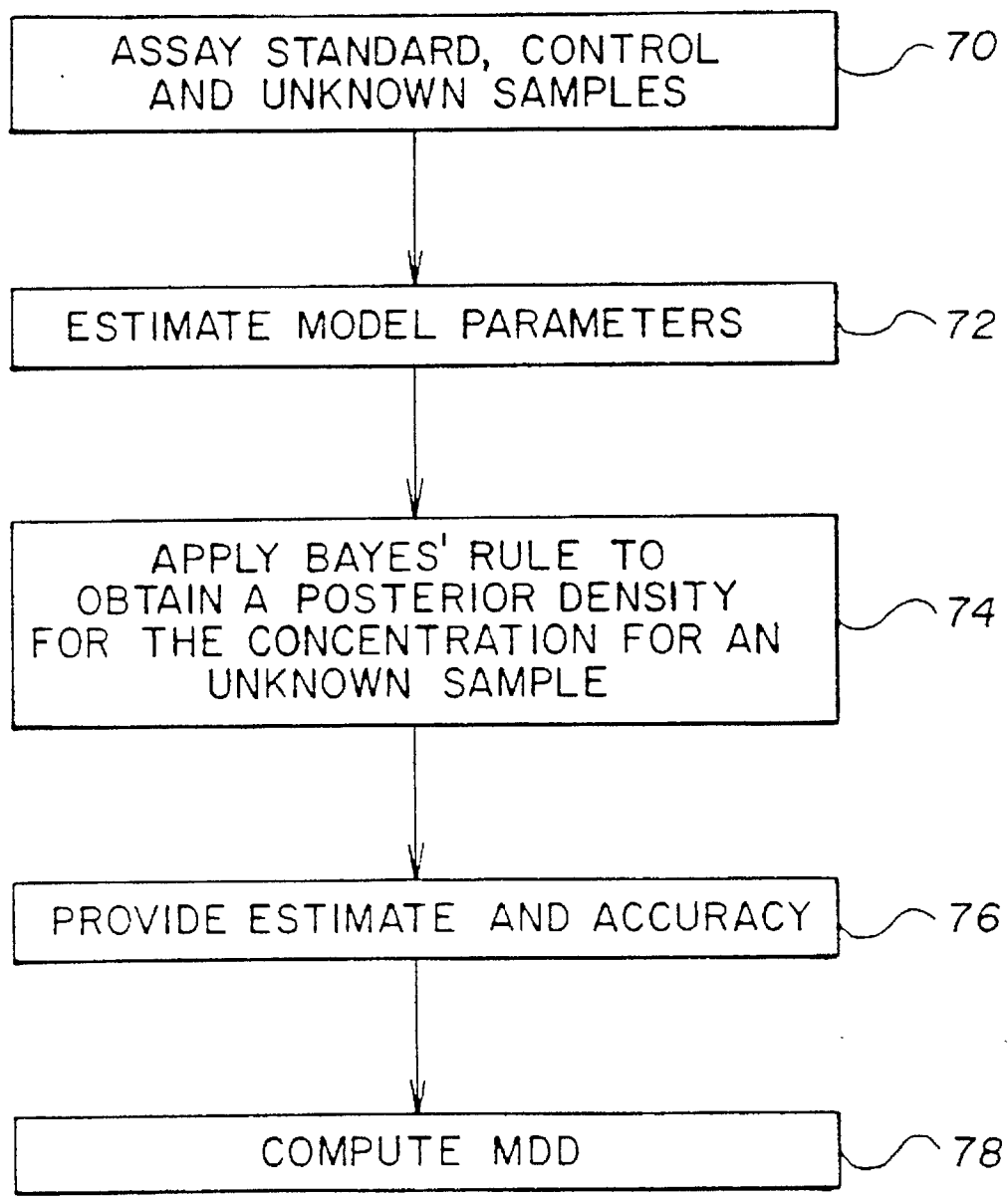
FIG. 4 is a flow chart describing how results of an assay run may be analyzed.
Figure 5:
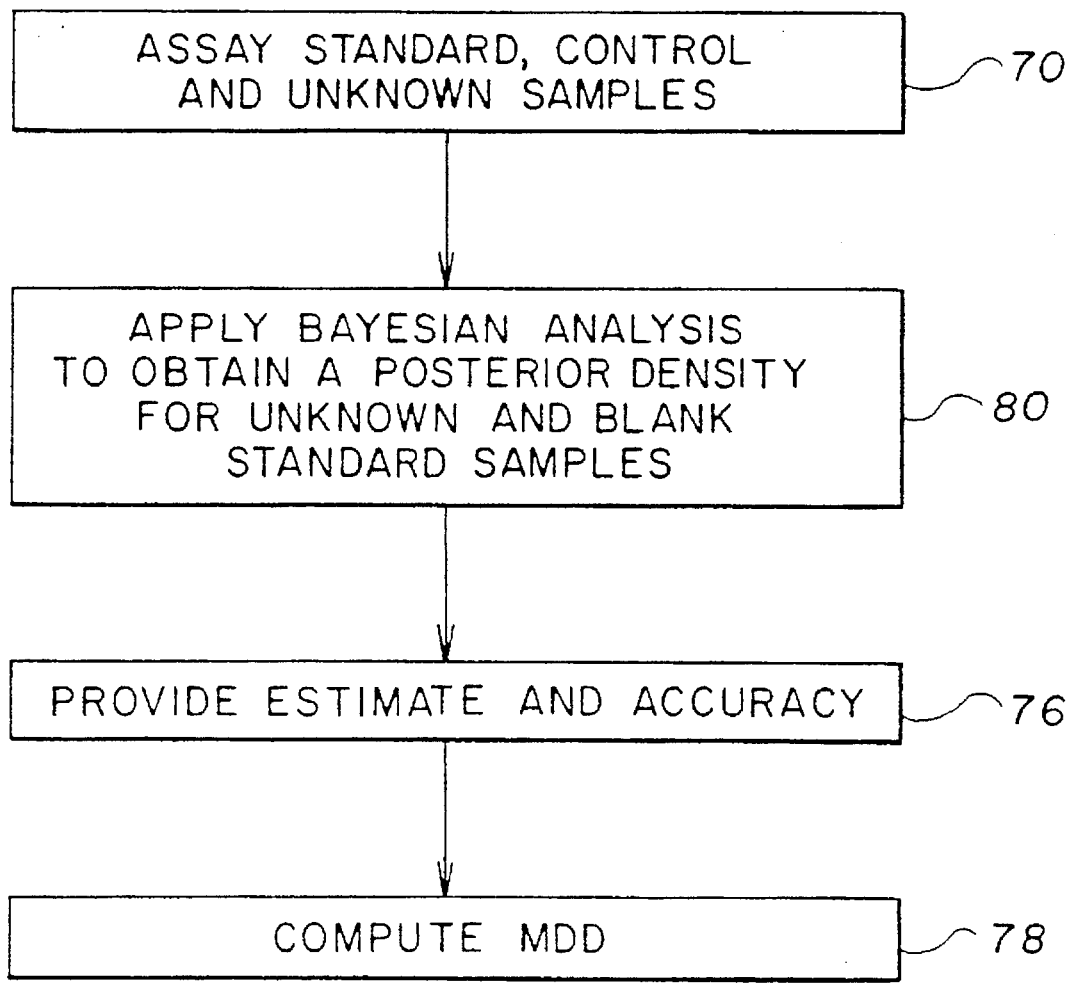
FIG. 5 is a flow chart describing a second embodiment of how results of an assay run may be analyzed.

In FIG. 4, the first step 70 of the method is to assay the standards, controls and unknown samples. The standards and controls are assayed at least in replicate. The unknowns may be assayed either in singlet, in duplicate or in as many replicates as considered appropriate. To reduce costs and to reduce the amount of waste resulting from an assay run, for example radioactive wastes from radioligand binding assays, the unknowns are preferably assayed in singlet.

Parameters for a standard curve for the assay are then estimated in step 72. This step involves the prescription of a suitable model of the expected response as a function of concentration and other parameters describing the model of the function, along with the estimation of those parameters. Although this step can be performed using conventional models for the standard curve, and conventional estimation procedures, it is also possible to use different models and estimation procedures.

Prescription of a Model For the Standard Curve

A reasonable prescription of a model for the expected response as a function of concentration and other parameters defined by the physical properties of the assay is typically provided by the mass-action law for the underlying chemical reaction of the assay. A difficulty with using the mass-action law has been that it does not always describe the empirical relation between the response and analyte concentration. (See Raab) However, it is expected that, as the purity and specificity of reagents improves, the mass-action law may be more appropriate to use as a model of this expected response function. Otherwise, the standard 4-PL model is suitable. Other models having a sigmoid form or part thereof are also suitable.

It is preferable to supplement the model for the expected response with a parameter which accounts for experimental variation. A suitable model is either the relative error model of Rodbard or the polynomial model of Finney 1976, both described above. However, it is preferable to supplement the model of the expected response in such a way that the experimental error is explicitly modeled on the analyte concentration scale as a random variable. Assuming that each sample has a relative error $v=\log V$ due to experimental variation and that $v$ is a Gaussian random variable, the probability density of $v$ is $\phi(v|0, \sigma^2)$. The parameter $\sigma^2$ represents the experimental error variance and is assumed to be constant across all analyte concentrations for the standards, controls, and unknown samples. The significance of this representation of relative error is that it accounts for the fact that laboratory procedures used to prepare samples randomly perturb the concentrations by a relative amount $V$. Modeling experimental error as a random variable on the analyte concentration scale has the effect of making the probability distribution of the response for a given concentration a continuous mixture of random variables. For a model of a radioligand binding assay, in which experimental error is modeled as a Gaussian random variable, the probability distribution of the response for a given concentration is a Gaussian mixture of Poisson random variables. Therefore, the distribution of the response depends on a concentration $H$, parameters $\theta$ which describe the physical properties of the assay, and $\sigma^2$ which describes the experimental error as a random variable.

The formulation of the preferred model for the standard curve is thus as follows.

The probability density of the response measured from assaying using a radioligand binding assay the $k^{th}$ replicate of sample $j$ in group $i$ given $h_{ij}=\log(H_{ij})$, $v_{ijk}$ and $\theta$ is $$[Y_{ijk}|h_{ij}, v_{ijk}, \theta]=P(Y_{ijk}|g(h_{ij}+v_{ijk}, \theta)), \qquad (4)$$

and the joint density of $Y_{ijk}$ and $v_{ijk}$ given $h_{ij}$, $\theta$, and $\sigma^2$ is $$[Y_{ijk},v_{ijk}|h_{ij}, \theta,\sigma^2]=[Y_{ijk}|h_{ij},v_{ijk},\theta]\phi(v_{ijk}|0,\sigma^2), \qquad (5)$$

where $k=1, \ldots, q, j=1, \ldots, N_i$ and $i=1,2,3$. Integrating (5) with respect to $v_{ijk}$ yields the density of the response $$[Y_{ijk}|h_{ij},\theta, \sigma^2]=\int[Y_{ijk},v_{ijk}|h_{ij}, \theta,\sigma^2]dv_{ijk} \qquad (6)$$

which is a Gaussian mixture of Poisson random variables.

Estimation of Model Parameters

The standard curve is typically derived using the known concentrations (for the standard samples) and their responses, along with a non-linear, weighted least squares technique, as described above. Although this method may be used, an alternative is to include the concentrations and responses for the controls and the responses for the unknowns, and to estimate the parameters of the model of the standard curve using a maximum-likelihood estimation technique. An alternative, as will be described in more detail below, is to integrate out the parameters $\theta$ and $\sigma^2$ to account for all uncertainty in $\theta$ and $\sigma^2$ while deriving the inference for the concentration of an unknown sample.

The joint density of the response, where $\theta'$ represents $\theta$, and $\sigma^2$ if used, and log analyte concentrations in group $i$ is $$[Y_i, h_i|\Theta'] = \prod_{j=1}^{Ni} \prod_{k=1}^{q} [Y_{ijk}|h_{ij}, \Theta'][h_{ij}] \qquad (7)$$

for $i=1,2,3$. The joint density of $Y_1$, $Y_2$ and $Y_3$, given $\theta$ and $\sigma^2$, is $$[Y_1, Y_2, Y_3|\Theta'] = \prod_{i=1}^{3} \prod_{j=1}^{Ni} \int \prod_{j=1}^{2} [Y_{ijk}|h_{ij},\Theta'][h_{ij}]dh_{ij} \qquad (8)$$

where $[h_{ij}]$ are given by equations (9) and (10) or (11) as described below. The log-likelihood of $\theta$ and $\sigma^2$ is the log of equation (8) viewed as a function of $\theta$ and $\sigma^2$. The maximum likelihood estimate of $\theta$ and $\sigma^2$ can be readily computed from the log-likelihood, by finding the values of $\theta$ and $\sigma^2$ which maximize equation (8). Preliminary estimates for the models parameters may be obtained from the assay data, for example, by using the formulation described in Rodbard.

Large values for the estimate of $\sigma$ would warn the laboratory personal that the assay run was particularly affected by experimental error. The maximum likelihood estimate $\sigma$ is an estimate of the standard deviation of the log relative experimental error. The interpretation of this parameter is readily given by example. Suppose $\sigma=0.05$, then 95% of the time the variation introduced into the measurement of the analyte by experimental error is less than $\pm 10\%$. ($=\pm 1.96* [\exp(\sigma)-1]$).

The prior probability distribution $[h]$ for the standards and controls, for the purpose of maximum likelihood estimation of $\theta$ and $\sigma^2$, are as follows. The concentrations in these samples are known prior to assay, therefore, appropriate prior densities for the analyte concentration in these samples are $$[h] = \begin{cases} \delta, h = h_{ij} \\ 0, \text{otherwise,} \end{cases} \text{ and} \qquad (9)$$

for $j=1, \ldots, N_i$ and $i=1, 2$, where $\delta$ is the Kronecker delta function.

The prior density for unknowns is described in more detail below with equations (10) and (11).

Application of Bayes' Rule and Prior Density For Unknowns

Given the estimated maximum likelihood values for the parameters θ, and $\sigma^2$ if used, Bayes' rule is applied in step 74 (FIG. 4) to obtain a posterior probability distribution for the unknown concentration of a sample. Bayes' rule is a well-known tool of statistical analysis, and is described in many textbooks on probability and statistics, for example, *Fundamentals of Applied Probability Theory*, by Alvin W. Drake (New York: McGraw Hill Book Company, 1967), pages 250–257 ("Drake"). In order to use Bayes' rule, a well defined prior density for the unknown concentration must be specified.

For any established assay system a laboratory has information on the range and frequency of values previously reported for the analyte. Despite this information, samples containing unknown concentrations of analyte are analyzed as if any value in the biologically possible range of concentrations were equally likely. (See "Sensitivity, specificity, and cost-effectiveness of thyrotropin assay in the diagnosis of thyroid disease in ambulatory patients," by E. T. De los Santos et al., in *Archives of Internal Medicine*, Volume 149, 1989, pp. 526–532, ("De los Santos"), or "Monitoring therapy in patients taking levothyroxine," by M. Helfand et al., in *Annals of Internal Medicine*, Volume 113, 1990, pp. 450–454 ("Helfand"), or "Accelerated bone loss in hypothyroid patients overtreated with L-thyroxine," by G. M. Stall et al., in *Annals of Internal Medicine*, Volume 113, 1990, pp. 265–269 ("Stall").) With such an analysis, a given assay experiment can provide information independent from that already amassed from prior assays, the disease state of a patient or the efficacy of a therapeutic intervention.

This analysis suggests that the prior probability density for a sample with an unknown concentration of analyte is uniform on most of its support. The support of this density is defined largely by the working range of the assay, i.e., the range across which the assay can reliably detect any analyte concentration. This range is established when the assay is developed using information on the biological range of concentrations of the analyte coupled with theoretical guidelines and empiricism to decide how much of each chemical species, e.g. antibody, radiolabelled antigen, and buffer etc., should comprise the assay system. The working range of the assay is usually specified as the intervals of concentrations between the smallest and largest non-blank standard. To permit the MDD to be estimated for any single assay run which includes the apparently blank standards, the interval over which the prior density has uniform support must extend to a concentration below the smallest non-blank standard.

Given these considerations, the form of a prior probability density for any analyte concentration may be described by the following function:

$$[h] = \begin{cases} \kappa (1 + t^2/\nu)^{-(\nu+1)/2}, & h < h_l, \quad t = (h - h_l)/s \\ \kappa, & h_l \leq h \leq h_h, \\ \kappa (1 + t^2/\nu)^{-(\nu+1)/2}, & h > h_h, \quad t = (h - h_h)/s \end{cases} \quad (10)$$

where ν is the number of degrees of freedom for a t-density, $h_l$ is the log concentration of analyte resulting from a single molecule of the analyte being placed in the unit volume of the assay, $h_h$ is the log of twice the concentration of the assay's highest standard, $\kappa = 0.85/(h_h - h_l)$, $s = 0.15(h_h - h_l)/(0.85\nu^{1/2}B(\frac{1}{2}, \nu/2))$, and $B(\frac{1}{2}, \nu/2)$ is the beta function with parameters ½ and ν/2. The prior density has 85% of its mass distributed uniformly between $h_l$ and $h_h$, and has the tails of a t-density on ν degrees of freedom on either side of these two log concentrations where the remaining 15% of the mass is evenly divided. The log concentration $h_l$ is the log of the theoretical lower limit of the sensitivity of the assay since this is the smallest concentration that could be detected if there were no error in the assay system. The log concentration $h_h$ is more difficult to specify on theoretical grounds. For practical purposes it has been placed at the log of twice the concentration of the highest standard of the assay.

A suitable prior density may practically vary from the form described by equation (10). A suitable prior density can be described by a continuous function with a large variance, i.e., the standard deviation of the density represented on the concentration scale is greater than about one-quarter of the range of the support of the density, and has a support large enough to account for high concentrations and to allow computation of the MDD. Small changes in such a prior density should result in negligible differences in the inferences for the unknown concentrations. As an example of an alternative prior density, a uniform distribution may be defined on the concentration (H) scale such that $[H] = H_o^{-1}$ for $0 \leq H \leq H_o$, where $H_o = \exp(h_h)$; and zero otherwise. When transformed to the log-concentration scale, such a prior density would take the form $$[h] = \begin{cases} \dfrac{\exp(h)}{\exp(h_h)}, & \text{for } h < h_h \\ 0, & \text{otherwise,} \end{cases} \quad (11)$$

Posterior Density of the Analyte Concentration

The conditional density of the log analyte concentration given maximum likelihood estimates of θ and $\sigma^2$ if used, below represented as θ^, and the $j^{th}$ set of responses $Y_{ij} = [Y_{ijq}, \ldots, Y_{ijq}]^T$ in the group i is $$[h_{ij}|Y_{ij}, \theta\hat{}] = [Y_{ij}|h_{ij}, \theta\hat{}][h_{ij}]/[Y_{ij}|\theta\hat{}] \quad (12)$$

where $$[Y_{ij}|h_{ij}, \hat{\Theta}] = \prod_{k=1}^{q} [Y_{ijk}|h_{ij}, \hat{\Theta}] \quad (13)$$

and $$[Y_{ij}|\theta\hat{}] = \int [Y_{ij}|h_{ij}, \theta\hat{}][h_{ij}]dh_{ij} \quad (14)$$

for $i = 1,2,3$ and $j = 1, \ldots, N_i$ and q is the number of replicates. The log concentration scale is used because it allows a convenient description of a broad range of concentrations for an analyte.

The posterior density of the analyte concentration $H_{ij}$ given the responses $Y_{ij}$ and the parameters θ^ is derived by applying in equation (12) the transformation of variables $H_{ij} = \exp(h_{ij})$ to obtain the posterior probability density $$[H_{ij}|Y_{ij}, \theta\hat{}], \quad (15)$$

for $i = 1,2,3$ and $j = 1, \ldots, N_i$.

Given θ^ and $Y_{ij}$ for sample j in group i, equation (15) describes a posterior density from which inferences can be made about the analyte concentration associated to a given response.

It is worth noting that the posterior probability density for both the standards and the controls has two different forms. The first was described above in connection with the description of the maximum-likelihood estimates θ^. However, once θ^ is estimated, the accuracy of the assay in measuring specified standard and control analyte concentrations can be evaluated by computing the posterior densities for these two groups using the prior probability density for the unknowns defined in either of equations (10) or (11) instead of the prior density in equation (9).

Given a posterior density $[H|Y,\theta^\wedge]$ for an unknown analyte concentration $H_y$, the concentration of analyte in the respective unknown samples may be inferred or estimated in step 76 (FIG. 4). The accuracy of that inference or estimate can also be determined. In particular, given the posterior probability density $[H|Y_{ij},\theta^\wedge]$ for $i=1,2,3$ and $j=1,\ldots,N_i$, let $\mu_{ij}$, $\sigma_{ij}^2$ and $m_{ij}$ denote respectively its posterior mean, posterior variance and posterior median. The analyte concentration in the $j^{th}$ sample of group i is inferred to be $m_{ij}$ (because $m_{ij}$ is independent of the transformation between h and H). The mean or mode may also be provided as the inferred analyte concentration.

The accuracy of the estimate of the concentration, e.g., $m_{ij}$, is fully specified by the posterior density. A summary of this accuracy could be given by the coefficient of variation (which is $\sigma_{ij}/\mu_{ij}$), the standard deviation or other summaries of the dispersion of the posterior density.

Alternative Derivation of Posterior Densities

As described above, it is possible to integrate out the possible parameters of the standard curve, rather than to provide an estimate of them. This method accounts for uncertainty in the estimation of $\theta$ and $\sigma^2$. For this aspect of the invention, the posterior density of the parameters $\theta$ and $\sigma^2$ is given by the following equation (16) where $\theta'$ represents $\theta, \sigma^2$:

$$[\theta'|Y_1,Y_2,Y_3,h_1,h_2]\propto\Pi([Y_1,Y_2|h_1,h_2,\theta'])\int\Pi([Y_3|h_3,\theta'])[h_3]dh_3[\theta'|h_1,h_2] \quad (16)$$

where $[\theta'|h_{1,2}]$ is the prior distribution of $\theta'$ for a given assay in which the concentrations of the standards are specified, and $\Pi$ is the product over, respectively, all the assay samples within the standards and controls and all the assay samples within the unknowns.

To specify the prior distribution of $\theta'$, a large number of point estimates of $\theta'$ are taken from a corresponding large number of assay runs. To facilitate the use of this information in the determination of $[\theta']$, a multivariate Gaussian distribution is used to approximate this prior density. A multidimensional histogram which represents a prior probability density for $\theta'$ is formed using these estimates. A multivariate mean and a variance/covariance matrix of the estimates of $\theta'$ are determined. The multivariate mean and variance/covariance matrix of the multivariate Gaussian are taken to be the determined multivariate mean and variance/covariance matrix. Suitable transformation of each model parameter may be necessary to improve the degree to which the multivariate Gaussian is a good approximation for the prior probability density of $\theta'$. For example, in models including $\sigma^2$ such transformation is typically appropriate.

Gibb's sampling or the marginal-Pearson algorithms give a large number N of draws of $\theta'$ from the posterior of equation (16). These N draws need only be taken once, and can be used in the calculation of posterior densities for all unknown samples in a single assay run. These algorithms are described in, respectively, "Bayesion Computation via the Gibbs Sampler and Related Markov Chain Monte Carlo Methods", by A. F. M. Smith and G. O. Roberts, in *J. R. Statist. Soc.*, Vol. 55, No. 1, 1993, pp. 3–23, and "Laplacian and Uniform Expansions with Applications to Multidimensional Sampling", by S. J. Skates, PhD. Dissertation, University of Chicago, Department of Statistics, August 1987.

For each draw $\theta^*$, $[Y_3|h_3,\theta^*][h_3]$ is calculated as a function of $h_3$ and is normalized to obtain a posterior density. The inferential (posterior) density for $h_{3j}$ is:

$$[h_{3j}|Y_1,Y_2,h_1,h_2,Y_{3j}]=\int[h_{3j}|Y_{3j},\theta'][\theta'|Y_1,Y_2,h_1,h_2,Y_3]d\theta' \quad (17)$$

where $[h_{3j}|Y_{3j},\theta']$ is the predictive density of $h_{3j}$ for a given $\theta^*$, and $[\theta'|Y_1,Y_2,h_1,h_2,Y_3]$ is the posterior distribution of $\theta'$ given the assay data.

To calculate the predictive density for given $\theta^*$ we have:

$$[h_{3j}|Y_1, Y_2, h_1, h_2, Y_3, \Theta'] = \frac{[Y_{3j}|h_{3j},\Theta^*][h_3]}{\int[Y_{3j}|h_{3j}, \Theta][h_3]d\Theta} \quad (18)$$

The integral in (18) is approximated by an average of the predictive densities $[h_{3j}|Y_{3j},\theta^*][h_3]$. Finally, to express this posterior density on the concentration scale we use the exponential transformation analagous to equation 15. The average value of the $\sigma$ component of the N $\theta^*$'s may be used as a point estimate of the standard deviation of the log relative experimental error. The average density of all N densities is the final density of log analyte concentration for an unknown sample given the assay result data.

Minimal Detectable Dose For An Assay Run

The minimal detectable dose for an assay run is determined in step 78, in accordance with the following definition. Given $0<\alpha<1$, and a posterior density for the analyte concentration $H_{y|0}$ corresponding to the assay of the apparent blank concentration standards, let E denote the set of random variables $H_y$ which satisfy the condition that zero is the left endpoint of the 1-$\alpha$ HPD of the random variable $H_y-H_{y|0}$. If $E_m$ denotes the set of medians of the probability densities of the random variables in E, then the minimal detectable dose of the assay is the supremum of $E_m$. Typically $\alpha=0.05$ or less. For computational purposes the supremum is the maximum.

Estimation of Extra-Poisson Variation

A quick preliminary calculation of the amount of extra-Poisson variation is provided by the approximate z-statistic. For the pair j in group i.

$$z_{ij}=2^{1/2}(Y_{ij2})/(Y_{ij1}+Y_{ij2})^{1/2}. \quad (19)$$

If the approximate z-statistics exceed an absolute value of four, there is a marked amount of extra-Poisson variation.

Computer System Implementation

A computer system which implements the method described above is preferably divided into a number of modules which perform different procedures. A data flow diagram of a suitable computer system and modules within the program, is provided in FIG. 6.

Figure 6:
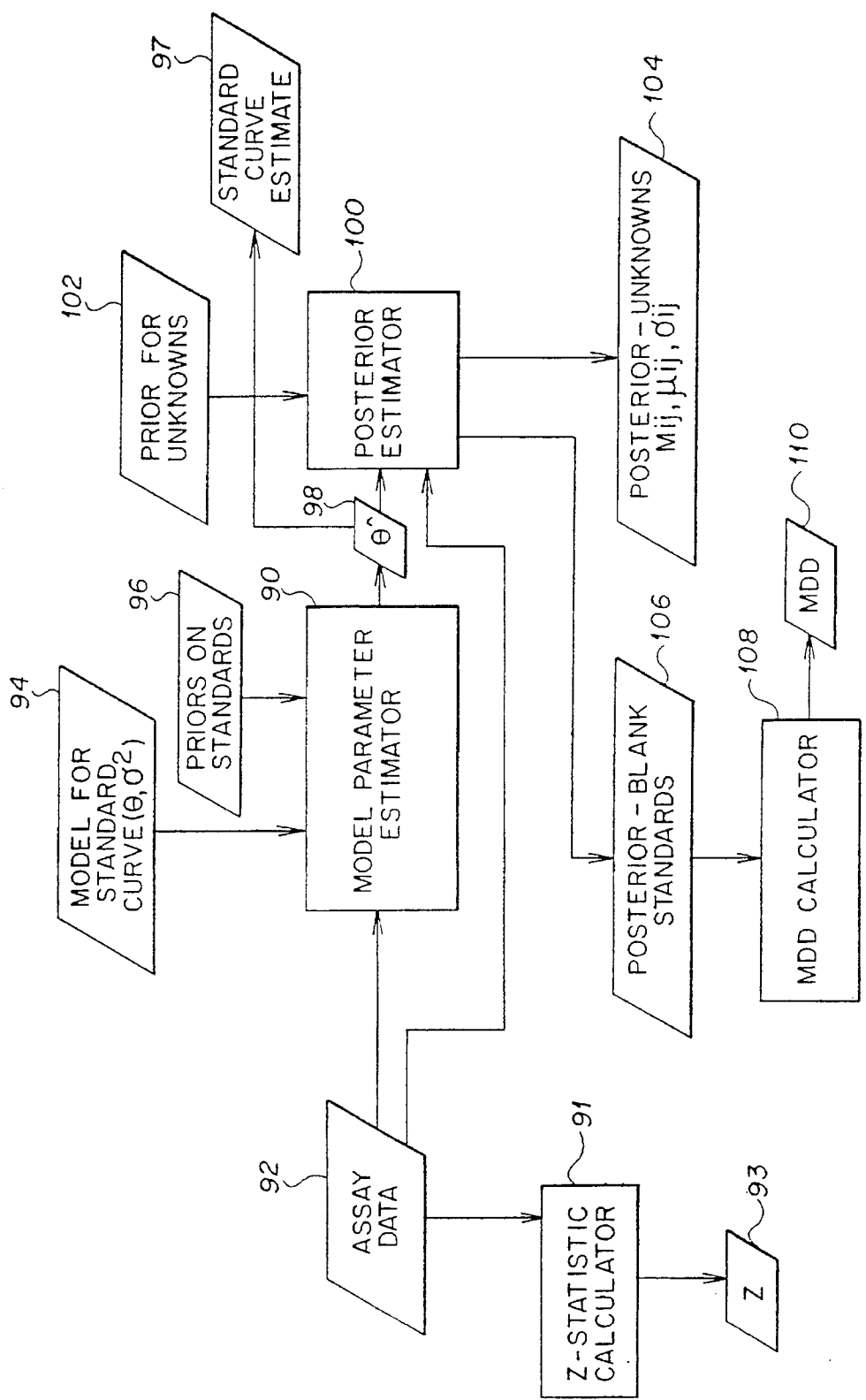
FIG. 6 is a dataflow diagram of a computer system which performs analysis on assay data.

In FIG. 6, a model parameter estimator 90 receives assay data 92, a model 94 for the standard curve, and prior densities 96 for the standards and controls. The model and the prior densities a typically provided by the user of the system. The assay data may come directly from the detector 40 (FIG. 2) or may have been stored in the memory 60 or 52 of the computer 42 in the interim. In some cases, the assay data may have been stored from prior assay runs which used conventional techniques for measuring the concentration of unknown samples, and therefore could not, for example, measure the accuracy of unknown samples assayed in singlet. Using the procedures outlined above, the model parameter estimator 90 determines an estimate 98 ($\theta^\wedge$) of the parameters $\theta$ and, if used, $\sigma^2$. Given $\theta^\wedge$, the estimated standard curve 97 for the assay is determined.

A z-statistic calculator 91 allows a quick preliminary estimate z 93 of extra-Poisson variation to be made, using the procedures outlined above.

A posterior estimator 100 receives the estimates 98, assay data 92 and a prior density 102 for the unknowns. Using the procedures outlined above, the posterior estimator 100 provides a posterior density 104 for each of the unknown samples, from which estimates of the concentration such the median m or mean $\mu$ and estimates of the accuracy, such as the standard deviation σ and coefficient of variation σ/μ may be calculated. The posterior estimator 100 also determines the posterior density 106 for the apparently blank standards.

An MDD calculator 108 receives the posterior densities 106 for the apparently blank standards and determines, using the procedures outlined above, the minimal detectable dose (MDD) 110 for the assay run.

Figure 7:
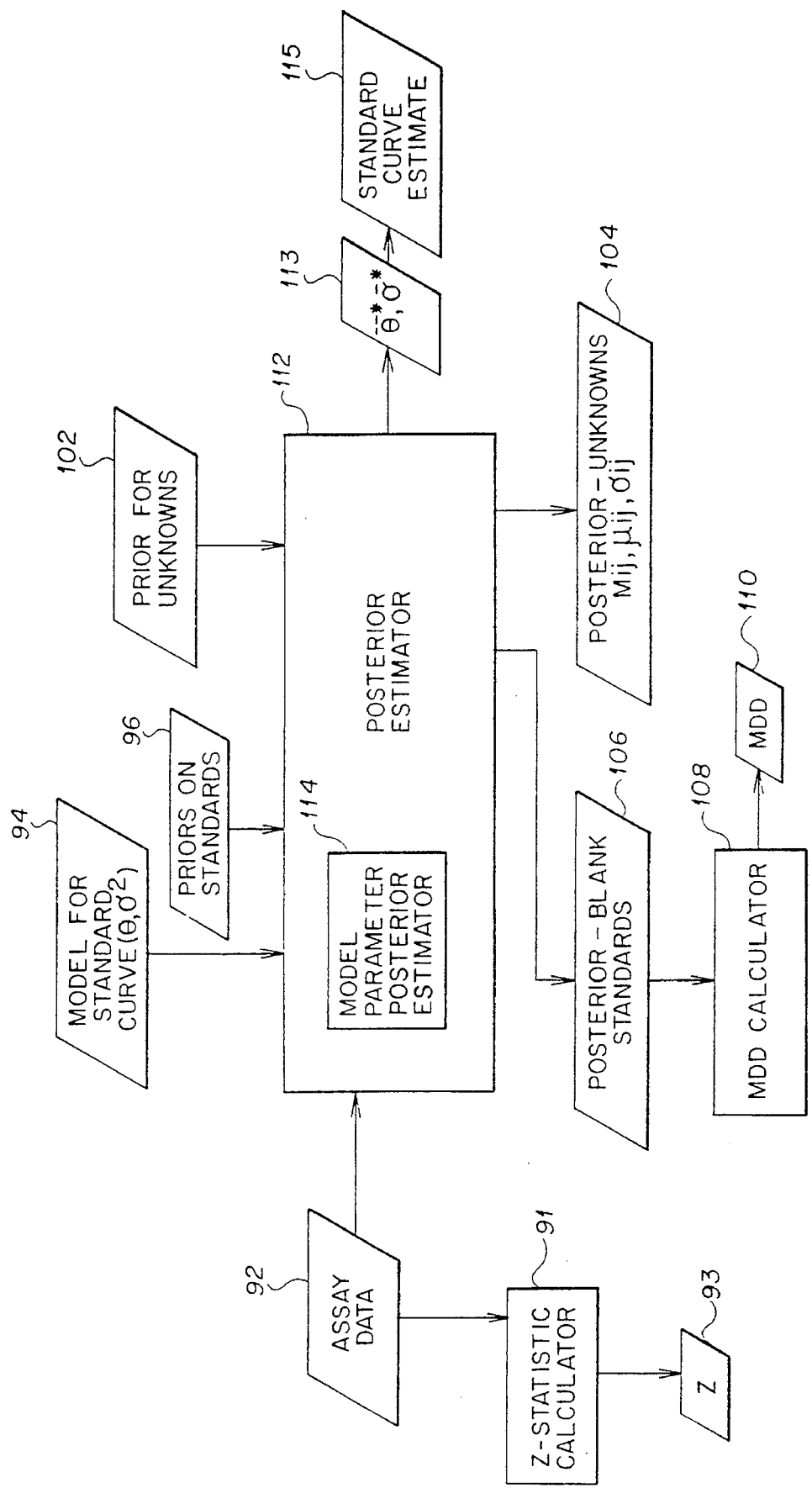
FIG. 7 is a dataflow diagram of a second embodiment of a computer system which performs analysis on assay data.

A similar data flow diagram for a second embodiment of the invention is shown in FIG. 7. In this embodiment, there is no model parameter estimator 90, but rather posterior estimator 112 includes a model parameter posterior estimator 114 which integrates out the model parameters while calculating the posterior densities using the procedures outlined above. In this process, an estimate θ*avg of the model parameters θ, and $\sigma^2$ if used, is provided from which an estimated standard curve 115 is determined. This embodiment is otherwise similar to the first embodiment.

A module dependency diagram, illustrating how different modules of the first embodiment of the computer system described above are interrelated, is illustrated in FIG. 8.

Figure 8:
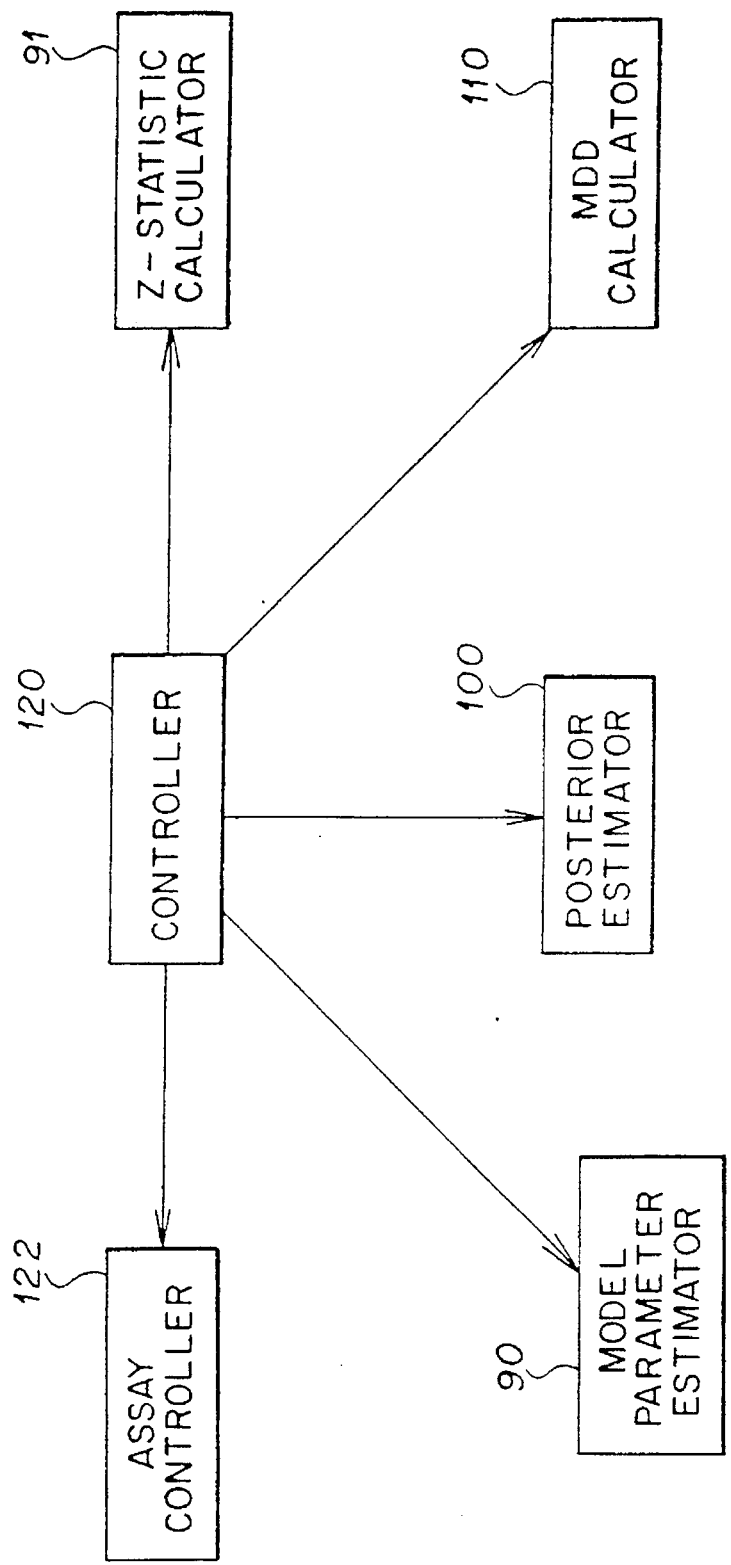
FIG. 8 is a module dependency diagram illustrating how different modules of the embodiment of the computer system of FIG. 6 are interrelated.

In FIG. 8, a controller 120 provides interaction with a user and an assay controller 122, allowing a user to specify which assay results are to be analyzed. The assay controller 122 is a conventional assay controller which is used to obtain raw response data from an assay run. The controller 120, after receiving assay data enables the model parameter estimator 90 to determine an estimate of the model parameters. When the model parameter estimator has completed its operations, the controller 120 enables the posterior estimator 100 to estimate posterior densities for the unknowns and blank standards. Finally, the controller 120 enables the MDD calculator 110 to determine the MDD of the assay run, and then provides the results to the user via an output of the computer 42.

Figure 9:
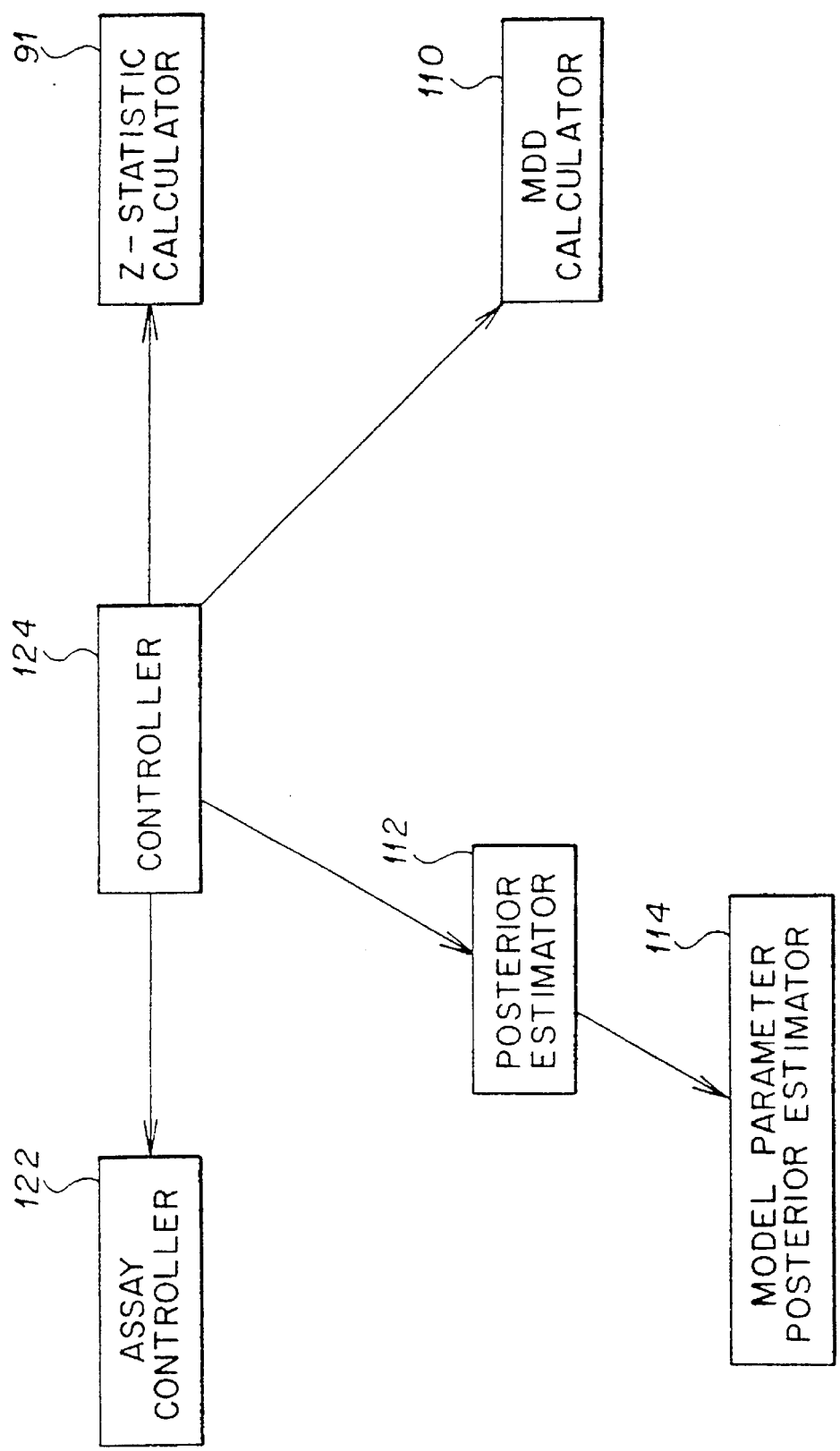
FIG. 9 is a module dependency diagram illustrating how different modules of the embodiment of the computer system of FIG. 7 are interrelated.

A module dependency diagram, illustrating how different modules of the second embodiment of the computer system described above are interrelated, is illustrated in FIG. 9.

In this embodiment, the controller 124 is slightly different from controller 120 of FIG. 8, in that it controls a different posterior estimator 112 (FIG. 7). The posterior estimator 112 controls the model parameter posterior estimator 114 in order to integrate out over the model parameters while determining the posterior densities of the unknowns and blank standards. The operation of controller 124 is otherwise similar to that of controller 120.

EXAMPLE

Cortisol Radioligand Binding Assay Run

Figure 10:
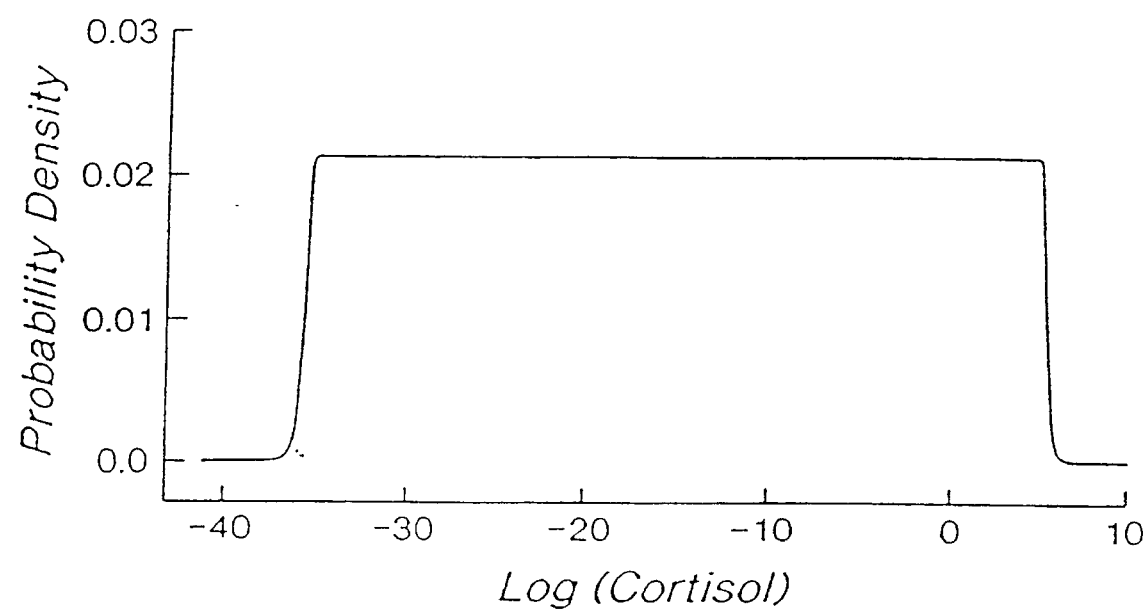
FIG. 10 is a graph representing a prior probability density for cortisol.
Figure 14A:
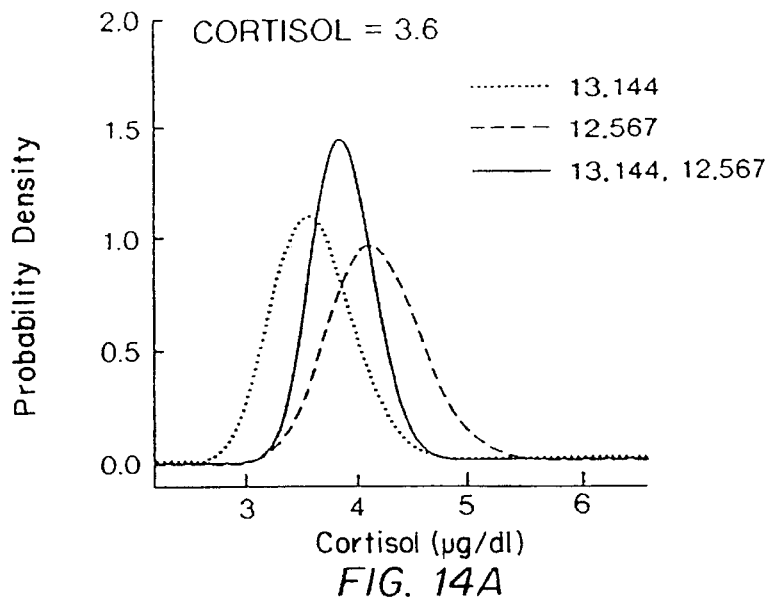
FIG. 14A–FIG. 14C are graphs representing the posterior density of the cortisol controls.
Figure 14B:
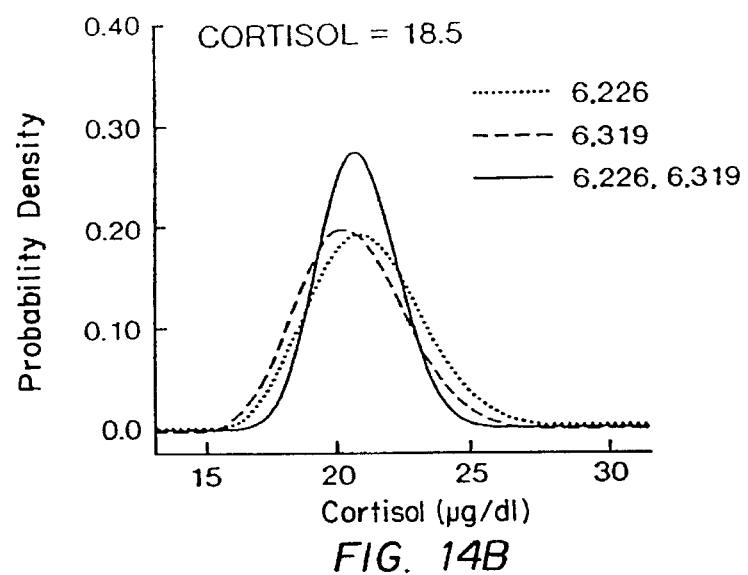
Figure 14C:
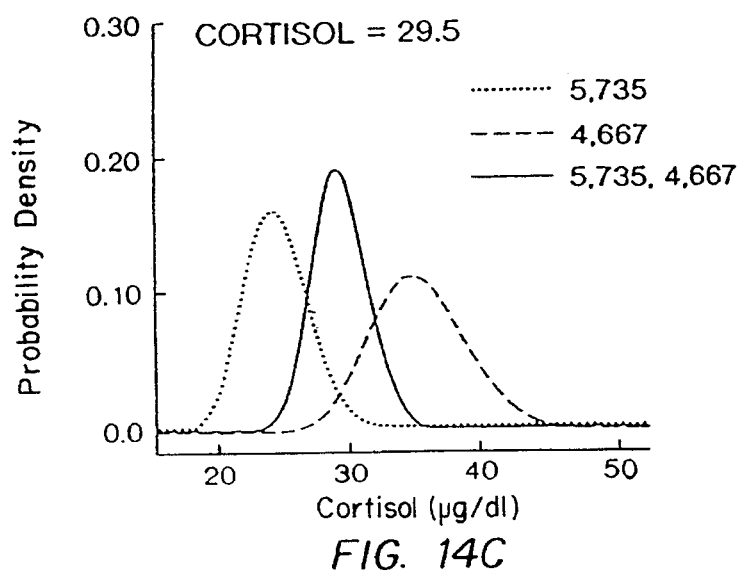

Cortisol, a steroid hormone produced by the adrenal glands, is responsible for regulating metabolism, the immune system and the stress response of the body. The plasma concentration of cortisol is generally reported in units of micrograms per deciliter (μg/dl) and its physiologic range under nonstress conditions extends from 3 to 24 μg/dl. In cases of Cushing's syndrome or high estrogen states, the plasma concentrations may be as high as 40 to 60 μg/dl. The working range of the cortisol assay extends from 1 to 60 μg/dl. Since the weight of one cortisol molecule is 6.02× $10^{-16}$ μg it follows that $h_l$=−35.05. Because the largest concentration for a standard sample is 60 μg/dl, $h_h$ was set to be 4.79. The prior probability density for cortisol using these specifications with ν=6 in equation (10) is shown in FIG. 10.

The example assay data consist of six cortisol standards prepared at concentrations of 0, 1, 3, 10, 25, and 60 (μg/dl) and their associated responses (measured in the number of radioactive counts); three control cortisol samples at concentrations 3.6, 18.5, and 29.5 (μg/dl) and their associated responses and the responses from 10 samples containing unknown concentrations of cortisol. All samples were assayed in duplicate. The table of FIG. 11 shows the data and the amount of extra-Poisson variation in each pair.

Four of the six standard response pairs, two of the three control response pairs and three of ten unknown response pairs have approximate z-statistics which exceed four in absolute value suggesting that this assay run has a marked amount of extra-Poisson variation and hence, experimental error.

To obtain preliminary parameter estimates, the Rodbard form of the 4-PL model was used. The value of "max" was set to be equal to the largest observed response plus 5% and "min" was set to be equal to the smallest observed response minus 5%. Using all the standard and control pairs except those corresponding to the apparently blank standards, preliminary estimates of ε and ρ (see equation 3) in the Rodbard formulation were computed by ordinary least squares, ignoring for the present the experimental error in the prepared hormone samples. These preliminary estimates were used as starting values for fitting the model of the standard curve without experimental error to the standard and control data by maximum likelihood estimation. These maximum likelihood estimates of the parameters were then used along with different starting values for the experimental error variance $\sigma^2$ to fit the full model to the standards, controls, and unknowns. The negative of the log-likelihood in equation (9) is minimized, for example by using the IMSL subroutine DBCONF with the integration in equation (6) being computed by an algorithm based on Laplace's method.

The Laplace method used in this example is described in the Appendix, and relies on *Inference and Disputed Authorship: The Federalist*, by F. Mosteller et al., (Reading, Mass.: Addison-Wesley, 1964), p. 154, ("Mosteller") and *Asymptotics and Special Functions*, by F. W. J. Olver, (New York: Academic Press, 1974), pp. 43 and 155, ("Olver").

Observed information matrices and standard errors were computed using the procedures described in "Computing observed information by finite differences," by R. E. Kass, in *Communications in Statistics-Simulations*, Volume 16, 1987, pp. 587–599. These procedures provide information describing how the assay data contribute to parameter estimates, as will now be described.

The model parameter estimates and their standard errors are given in the table in FIG. 12. To assess the value of using the controls and the unknowns along with the standards to estimate the model parameters, the table in FIG. 12 shows the diagonal elements of the observed information matrix decomposed into individual additive components from the standards, the controls and the unknowns.

The controls contribute information to the estimation of θ and $\sigma^2$, and in fact, the percentages of information obtained from the controls for estimating γ and $\sigma^2$ are greater than those obtained from the standards. These percentages for γ are 86.24% from the controls compared with 11.87% from the standards and for $\sigma^2$, 43.1% compared with 34.33%.

The unknowns contribute 22.57% of the information for the estimation of $\sigma^2$, and therefore, should be included in the analysis to determine better the magnitude of this parameter. As expected, the unknowns provide negligible information for the estimation of θ. The interpretation of σ for this example assay run is that the experimental error was less than ±20% (=±1.96 * {exp (σ)−1}) for most (95%) of the assay samples. This information cannot be obtained using conventional methods.

FIGS. 13A–13F and 14A–14C show the plots of the posterior densities of the standards and controls based on the observed single responses and on observed response pairs. The summary statistics for these densities are given in the table of FIG. 15. The plots in FIGS. 13 and 14 and the results in these tables show that the posterior densities based on either the single or paired responses are symmetric with a small right skew in that, for each, the median exceeds the mode and both are less than the mean. The percentage coefficient of variation for the single response posterior densities range from 10.1% to 17.9% and from 7.1% to 10.0% for those based on response pairs.

All the individual posterior medians approximate reasonably well the intended cortisol concentrations for the standards and the controls with the exception of those corresponding to the posterior density based on the first response, 18,747, for the control with an apparently blank concentration, and the single response posterior density for the response of 9,857 corresponding to estimating the second control with an intended cortisol concentration of 10 μg/dl. The respective medians are 0.50 and 8.08. The estimates of each based on the paired response posterior densities, 0.35 and 8.76, respectively are closer to the intended concentrations. The table in FIG. 16 shows the summary statistics for the posterior densities for the unknowns and the MDD. The coefficients of variation for unknowns have the same pattern as that for the standards and controls.

Figure 17:
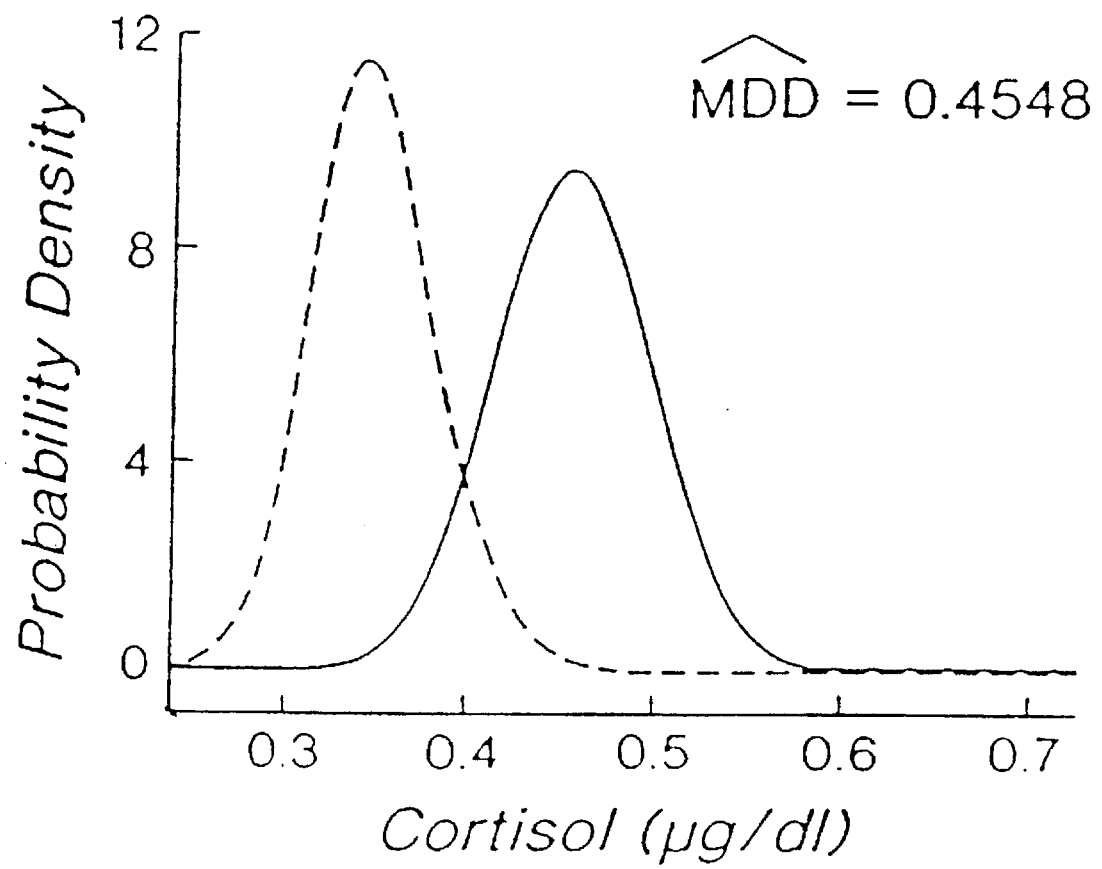
FIG. 17 is a graph representing the relationship between the posterior densities of the zero cortisol concentration and of the minimal detectable dose of the example cortisol assay run.

If $\alpha$ is 0.05 in the calculation of the MDD, then the estimated MDD or sensitivity is 0.45. The relationship between the posterior density whose median is the estimated MDD and the posterior density corresponding to the responses obtained from assaying the apparently blank standards is shown in FIG. 17.

Discussion

One advantage of the method of the present invention is that the estimates using Bayes' rule consider explicitly the distribution of the analyte given the responses. By developing a prior density for the analyte concentration based on known properties of the assay and modeling specifically the experimental error, this method offers several other distinct advantages.

First, by modifying the model of the standard curve to characterize explicitly the experimental error on the analyte concentration scale instead of on the response scale, this source of error can be separately identified as uncertainty in the analyte in any assay data analysis.

Second, the use of the unknowns and the controls along with the standards in the estimation of $\theta$ and $\sigma^2$ allows the magnitude of the experimental error to be determined more accurately. Furthermore, because the parameter $\sigma^2$ is the mean square relative experimental error, the estimate of the error can be understood more readily in terms of the assay than the exponent on the power function in the relative error model of Rodbard. When samples are assayed with more than one replicate, the approximate z-statistic may be used to identify the possible magnitude of the assay experimental error prior to any model fitting. For an analyte assayed with at least 3 replicates, this statistic could take the form $(Y_{ij,max}-Y_{ij,min})/Y_{ij,avg}^{1/2}$. The estimated experimental error variance has been found to increase with the number of samples whose approximate z-statistic exceeds four in absolute value.

Second, the prior density selected accurately summarizes the manner in which the laboratory chemist uses prior knowledge of the design of the assay and allows two objectives of the assay experiment to be accomplished: 1) the assay experiment is an independent source of information and 2) the MDD for the assay run may be computed.

The foregoing example also demonstrates that the bulk of the information on the concentration of analyte in a sample and its accuracy are provided by the data through the estimated probability density of the response (equation 6) and not by the prior density. That is, the interval of effective non-zero support of the posterior densities is markedly smaller than that of the prior density and the ratio of the heights of the posterior densities at the modes to that of the prior density at its mode ranges from 3 to 500 for the posterior densities based on singlets and from 5 to 550 for those based on replicates.

If the analysis of a given sample were to suggest that its analyte concentration might exceed the upper limit of the effective non-zero support of the prior density, then serial dilutions of the sample could be made and the analysis performed on the diluted samples. The appropriate error density of the original sample could then be computed from the posterior densities of the diluted samples by variable transformations.

A third advantage of this method is that, conditional on $\theta$, the posterior probability densities provide a complete description of the accuracy in a determination of an analyte concentration. The median of the posterior density was selected as the estimate of the analyte because this measure of location is invariant under transformation from h to H.

As a fourth advantage, it is now possible to compute a posterior density based on the responses for any number of replicates for a standard, control or unknown sample and therefore, to estimate the accuracy in specimens assayed as singlets. In addition, all the assay calibration statistics e.g., the coefficients-of-variation and the MDD, are maximum likelihood estimates characterized with respect to well-defined probability densities.

Fifth, the new definition of the MDD allows for a more accurate determination of the concentration of analyte which the assay can just distinguish from a blank concentration given that all specimens are assayed with error. That is, suppose, as part of a calibration experiment, that a set of $N_4$ dilutions of the smallest non-blank standard are assayed in addition to the typical set of standards and controls. For $j=1, \ldots, N_4$, let $H_y|H_{4j}$ denote the random variable associated with the posterior density obtained from assaying the $j^{th}$ dilution. Because each specimen is assayed with error, both the posterior densities of the $H_y$'s and those of the random variables $H_y-H_{y|0}$ are used. In this experiment the elements of E will come from the $H_y|H_{4j}$'s since it is unlikely that specimens whose intended concentrations exceed that of the smallest non-blank standard will satisfy the MDD definition above. The estimated analyte concentrations which are just stochastically different from an apparent blank belong to the set $E_m$ and if the number of replicates assayed for each specimen is one, then $E_m$ has a single element which is the MDD. If the number of replicates is greater than one, then $E_m$ has more than one element and the supremum of $E_m$ is chosen as the MDD.

Sixth, under this approach consideration of the accuracy of the blank sample concentration and any other sample concentration is made explicit by the $H_y-H_{y|0}$'s, therefore obviating the need to have three separate definitions of the MDD such as given by Oppenheimer. Since the MDD may be computed for any assay run which includes standards having apparently blank concentrations, any concentration detected between the MDD and the lowest non-blank standard can be reliably reported as part of the usual response analysis. Including dilutions of the lowest non-blank standard provides better definition of the behavior of the assay at lower concentrations and may increase the estimation precision of $\theta$ and a $\sigma^2$. How many dilutions to include is dependent on the experimental design.

Having now described a few embodiments of the invention, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention as defined by the appended claims and equivalents thereto.

APPENDIX

We derive the Laplace approximation to the Gaussian mixture of Poisson densities by the integral in (6) From Olver (1974, p.155) the Laplace approximation to the integral $$I = \int_{b_1}^{b_2} e^{-np(v)} q(v) dv \text{ is}$$

$$I \sim \frac{(2\pi)^{\frac{1}{2}}}{(np_2)^{\frac{1}{2}}} q(\hat{v}) e^{-np(\hat{v})} \left\{ 1 + \frac{f_2}{2n} + 0(n^{-2}) \right\},$$

where $$f_2 = \left( 12q_2 - \frac{12q_1 p_3}{p_2} - \frac{3q_0 p_4}{p_2} + \frac{5q_0 p_3^2}{p_2^2} \right) / (12 p_2),$$

and $p_i$, $q_i$ are respectively the $i^{th}$ derivatives of $p$ and $q$ evaluated at $\hat{v}$, where $\hat{v}$ is the point at which $p$ assumes its minimum on the interval $(b_1, b_2)$. For evaluating (6) we follow Mosteller and Wallace (1964, p.154) and set n=1. The logarithm of the integrand in (3.2) has components $$\log[Y_{ijk}/h_{ij}, v_{ijk}, \theta] = Y\log g - g - \log Y!, \log \phi(v_{ijk}/0, \sigma^2) = -v^2/(2\sigma^2) - (\log 2\pi)/2 - \log \sigma,$$

where $Y = Y_{ijk}$, $v = v_{ijk}$ and $g(h, \theta)$ is given by (2.1). Hence, using Stirling's approximation to the factorial function $\log Y! \sim (\log 2\pi)/2 + (Y+\frac{1}{2})\log Y - Y$, setting $p(v) = g(v) - Y\log\{g(v)\} + v^2/(2\sigma^2)$ and $q(v)=1$, the Laplace approximation to (6) is $$I \sim \frac{\exp\{(Y-g) + Y\log(g/Y) - (v^2/2\sigma^2)\}}{(2\pi Y p_2)^{\frac{1}{2}} \sigma} \{1 + f_2/2 + 0(n^{-2}) + \ldots\},$$

where $\hat{g} = g(\hat{v})$. The IMSL numerical minimization routine UVMID is used to determine $\hat{v}$. The importance of evaluating the term $f_2/2$ is both to establish that the asymptotics have taken effect, and to increase the accuracy of the approximation. A small value for the second term, $f_2/2$, compared to the first term, 1.0, indicates that the Laplace approximation is likely to be accurate (Olver, 1974, p.43). In the integrations performed as part of the data analysis in Section 5 this term was consistently on the order of $10^{-5}$. To evaluate $f_2$ and $p_2$ we require the derivatives of $p$ and $g$ with respect to $v$. These are $$\frac{\partial p}{\partial v} = \frac{\partial g}{\partial v} \left( 1 - \frac{Y}{g} \right) + \frac{v}{\sigma^2},$$

$$\frac{\partial^2 p}{\partial v^2} = \frac{\partial^2 g}{\partial v^2} \left( 1 - \frac{Y}{g} \right) + Y \frac{1}{g^2} \left( \frac{\partial g}{\partial v} \right)^2 + \frac{1}{\sigma^2},$$

-continued $$\frac{\partial^3 p}{\partial v^3} = \frac{\partial^3 g}{\partial v^3} \left( 1 - \frac{Y}{g} \right) +$$
$$Y \left\{ \frac{3}{g^2} \left( \frac{\partial g}{\partial v} \right) \frac{\partial^2 g}{\partial v^2} - \frac{2}{g^3} \left( \frac{\partial g}{\partial v} \right)^3 \right\},$$

$$\frac{\partial^4 p}{\partial v^4} = \frac{\partial^4 g}{\partial v^4} \left( 1 - \frac{Y}{g} \right) +$$
$$Y \left\{ \frac{6}{g^4} \left( \frac{\partial g}{\partial v} \right)^4 - \frac{12}{g^3} \left( \frac{\partial g}{\partial v} \right)^2 \frac{\partial^2 g}{\partial v^2} + \frac{3}{g^2} \left( \frac{\partial^2 g}{\partial v^2} \right)^2 + \frac{4}{g^2} \left( \frac{\partial g}{\partial v} \right) \frac{\partial^3 g}{\partial v^3} \right\}.$$

For the derivatives of g with respect to v, let $e=\exp(\beta-\gamma(h+v))$, $K=(\max - \min)e/(e+1)$ and $r=\gamma/(e+1)$, then we have $$\frac{\partial g}{\partial v} = Kr,$$

$$\frac{\partial^2 g}{\partial v^2} = Kr^2(e-1),$$

$$\frac{\partial^3 g}{\partial v^3} = Kr^3(1 - 4e + e^2),$$

$$\frac{\partial^4 g}{\partial v^4} = Kr^4(e-1)(1 - 10e + e^2).$$

What is claimed is:

1. A method for measuring a concentration of an analyte in a sample having an unknown concentration of the analyte using a binding assay in which a labelled binding partner for the analyte is allowed to react with the analyte to form a labeled complex in an assayed sample, wherein the labeled binding partner includes a tag which emits an experimental indicator and wherein the assayed sample emits in a predetermined period of time an amount of the experimental indicator, which amount is a response emitted by the assayed sample, the method comprising the steps of:

assaying a plurality of known samples using the binding assay, wherein each known sample has a known concentration of the analyte and is allowed to react with the labeled binding partner for the analyte to form a first labeled complex and the first labeled complex is detected to obtain a response emitted by each assayed known sample;

assaying the unknown sample using the binding assay, wherein each unknown sample is allowed to react with the labeled binding partner for the analyte to form a second labeled complex and the second labeled complex is detected to obtain a response emitted by the assayed unknown sample;

supplying a prior probability density for the unknown concentration and a probability model which specifies a standard curve relating an expected response to a concentration of the analyte;

generating a posterior density for the unknown concentration based on the supplied prior density, the supplied probability model, and the responses for the assayed known samples and the assayed unknown sample, by applying Bayes' rule; and providing a characteristic of the posterior density as a measure of the concentration of the analyte in the unknown sample.

2. A method for measuring a concentration of an analyte in a sample having an unknown concentration of the analyte using a competitive binding assay in which a the analyte and a labeled competitor of the analyte are allowed to react with a binding partner for the analyte, wherein the labeled competitor includes a tag which emits an experimental indicator, wherein the analyte and the labeled competitor compete with one another for binding to the binding partner to form a labeled complex in an assayed sample, wherein the assayed sample emits in a predetermined period of time an amount of the experimental indicator, which amount is a response emitted by the assayed sample, the method comprising the steps of:

assaying a plurality of known samples using the competitive binding assay, wherein each known sample has a known concentration of the analyte and is allowed to react with the binding partner and the labeled competitor to form a first labeled complex and the first labeled complex is detected to obtain a response emitted by each assayed known sample;

assaying the unknown sample using the competitive binding assay, wherein each unknown sample is allowed to react with the binding partner and the labeled competitor to form a second labeled complex and the second labeled complex is detected to obtain a response emitted by the assayed unknown sample;

supplying a prior probability density for the unknown concentration and a probability model which specifies a standard curve relating an expected response to a concentration of the analyte;

generating a posterior density for the unknown concentration based on the supplied prior density, the supplied probability model, and the responses for the assayed known samples and the assayed unknown sample, by applying Bayes' rule; and providing a characteristic of the posterior density as a measure of the concentration of the analyte in the unknown sample.

3. The method of claim 1 or claim 2, wherein the posterior density has a dispersion, a coefficient of variation, a variance, and a resolution, and further comprising the step of providing a measure of accuracy of the provided measure of concentration, wherein the measure of accuracy is one of a summary of the dispersion, the coefficient of variation, the resolution and the variance.

4. The method of claim 1 or claim 2, further comprising the step of providing a measure of accuracy of the measure of concentration of the analyte, wherein the measure of accuracy is defined in terms of the posterior density.

5. The method of claim 1 or claim 2, further comprising the step of determining a minimal detectable dose, thereby defining a lowest analyte concentration which can be detected.

6. The method of claim 4, further comprising the step of decomposing the measure of accuracy into an experimental error and a response error.

7. The method of claim 1 or claim 2, wherein the posterior density is determined using estimated parameters of the supplied probability model.

8. The method of claim 7, wherein the estimated parameters are determined using a weighted least-squares technique and using the responses obtained for the known samples.

9. The method of claim 7, wherein the estimated parameters are determined using maximum likelihood estimation and using the responses obtained for the known samples.

10. The method of claim 7, wherein the estimated parameters of the probability model are derived using the responses for the known samples and the unknown sample.

11. The method of claim 7, wherein the estimated parameters are derived using the responses for the known samples.

12. The method of claim 7, further comprising the step of integrating out the estimated parameters of the probability model to account for uncertainty in these parameters while deriving an inference for the measure of the analyte concentration of the unknown sample.

13. The method of claim 1 or claim 2, wherein the probability model has a standard curve which is derived from a mass-action law for an underlying chemical reaction of the binding assay.

14. The method of claim 1 or claim 2, wherein the probability model used to specify the standard curve includes a random variable which represents variations in concentration of analyte due to variability in preparation of samples, whereby the posterior density is a mixture of random variables.

15. The method of claim 5, further comprising the step of determining a posterior density for apparently blank known samples, and a highest probability density interval having a left endpoint and a right endpoint, such that the minimum detectable dose is a maximum value of a set of medians of probability densities of random variables $H_y$ for which zero is the left endpoint of the highest probability density interval of random variables $H_y$-$H_{y|0}$.

16. The method of claim 1, wherein the step of assaying a known sample includes the steps of:

mixing the known sample with the labeled binding partner to allow the analyte and the labeled binding partner to react and to form the first labeled complex;

separating the first labeled complex from other material; and detecting the response emitted by the first labeled complex as the response emitted by the known sample.

17. The method of claim 1, wherein the step of assaying an unknown sample includes the steps of:

mixing the unknown sample with the labeled binding partner to allow the analyte and the labeled binding partner to react and to form the first labeled complex;

separating the first labeled complex from other material; and detecting the response emitted by the first labeled complex as the response emitted by the unknown sample.

18. The method of claim 2, wherein the step of assaying a known sample includes the steps of:

mixing the known sample with the binding partner and the labeled competitor to allow the analyte and the labeled competitor to compete for the binding to the binding partner;

separating bound material from unbound material; and detecting the response emitted by the bound material as the response emitted by the known sample.

19. The method of claim 2, wherein the step of assaying an unknown sample includes the steps of:

mixing the unknown sample with the binding partner and the labeled competitor to allow the analyte and the labeled competitor to compete for the binding to the binding partner;

separating bound material from unbound material; and detecting the response emitted by the bound material as the response emitted by the unknown sample.

20. A system for measuring a concentration of an analyte in a sample having an unknown concentration of the analyte using a binding assay including a labeled binding partner having a tag which emits an experimental indicator and wherein an assayed sample emits, in a predetermined period of time, an amount of the experimental indicator, which amount is a response emitted by the assayed sample, comprising:

a detector arranged to detect the response of the assayed sample, and providing an output indicative of the response detected; and a computer system having an input connected to receive the output from the detector, and including a memory and a processing unit, the memory having stored therein a prior probability density for the unknown concentration and a probability model which specifies a standard curve relating an expected response to a concentration of the analyte, the processing unit including:

means for controlling the binding assay and the detector to detect a response of a plurality of known samples and the unknown sample in the predetermined period of time;

means for generating a posterior density for the unknown concentration based on the stored prior density, the stored probability model, and the responses for the known samples and the unknown samples, by applying Bayes' rule; and means for communicating a characteristic of the posterior density as a measure of the concentration of analyte in the unknown sample.

21. The system of claim 20, wherein the posterior density has a dispersion, a coefficient of variation, a variance, and a resolution, and further comprising means for communicating a measure of accuracy of the measure of concentration, wherein the measure of accuracy is one of a summary of the dispersion, the coefficient of variation, the resolution and the variance.

22. The system of claim 20, further comprising means for communicating a measure of accuracy of the measure of concentration of the analyte, wherein the measure of accuracy is defined in terms of the posterior density.

23. The system of claim 20, further comprising means for determining a minimal detectable dose, thereby defining a lowest analyte concentration which can be detected.

24. The system of claim 22, further comprising means for decomposing the measure of accuracy into an experimental error and a response error.

25. The system of claim 20, wherein the posterior density is determined using estimated parameters for the supplied probability model.

26. The system of claim 25, wherein the estimated parameters are determined using a weighted least-squares technique and using the responses obtained for the known samples.

27. The system of claim 25, wherein the estimated parameters are determined using maximum likelihood estimation and using the responses obtained for the known samples.

28. The system of claim 25, wherein the estimated parameters are derived using the responses for the known sample and the unknown samples.

29. The system of claim 25, wherein the estimated parameters are derived using the responses for the known samples.

30. The system of claim 25, further comprising means for integrating out the estimated parameters of the probability model to account for uncertainty in these parameters while deriving an inference for the measure of the analyte concentration of the unknown sample.

31. The system of claim 20, wherein the probability model specifies a standard curve which is derived from a mass-action law for an underlying chemical reaction of the binding assay.

32. The system of claim 20, wherein the probability model includes a random variable which represents variations in concentration of analyte due to variability in preparation of samples, whereby the posterior density is a mixture of random variables.

33. The system of claim 20, further comprising means for determining a posterior density for apparently blank known samples, and a highest probability density interval having a left endpoint and a right endpoint, such that the minimum detectable dose is a maximum value of a set of medians of probability densities of random variables $H_y$ for which zero is the left endpoint of the highest probability density intervals of the random variables $H_y$-$H_{y|0}$.

34. The method of claim 3, further comprising the step of decomposing the measure of accuracy into an experimental error and a response error.

35. The system of claim 21, further comprising means for decomposing the measure of accuracy into an experimental error and a response error.

* * * * *